United States Patent
Ben-Ezra et al.

(10) Patent No.: US 10,610,294 B2
(45) Date of Patent: Apr. 7, 2020

(54) DEVICES AND METHODS FOR TRANSURETHRAL BLADDER PARTITIONING

(71) Applicant: NewUro, B.V., Amsterdam (NL)

(72) Inventors: Omry Ben-Ezra, Tel-Aviv (IL); Itzhak Avneri, Tel-Aviv (IL); David Staskin, Boston, MA (US); Roger A. Stern, Cupertino, CA (US); Jerome Jackson, Los Altos, CA (US); Benjamin Wang, San Leandro, CA (US)

(73) Assignee: NewUro, B.V., Amsterdam (NL)

( * ) Notice: Subject to any disclaimer, the term of this patent is extended or adjusted under 35 U.S.C. 154(b) by 705 days.

(21) Appl. No.: 15/179,623

(22) Filed: Jun. 10, 2016

(65) Prior Publication Data
US 2016/0331450 A1 Nov. 17, 2016

Related U.S. Application Data

(63) Continuation-in-part of application No. 14/519,933, filed on Oct. 21, 2014, now Pat. No. 9,883,906, which
(Continued)

(51) Int. Cl.
*A61B 18/14* (2006.01)
*A61M 19/00* (2006.01)
(Continued)

(52) U.S. Cl.
CPC .......... *A61B 18/1492* (2013.01); *A61B 1/307* (2013.01); *A61M 19/00* (2013.01);
(Continued)

(58) Field of Classification Search
CPC ........ A61B 18/1492; A61B 2018/0016; A61B 2018/00214; A61B 2018/0022;
(Continued)

(56) References Cited

U.S. PATENT DOCUMENTS

| 4,808,164 A | 2/1989 | Hess |
| 5,056,531 A | 10/1991 | Shimoyama |

(Continued)

FOREIGN PATENT DOCUMENTS

| WO | WO 2005/067791 A1 | 7/2005 |
| WO | WO-2011022897 A1 | 3/2011 |

(Continued)

OTHER PUBLICATIONS

Essenhigh, D. M. and Yeates, W. K. Transection of the bladder with particular reference to enuresis. British Journal of Urology. 1973; 45: 299-305.
(Continued)

*Primary Examiner* — Michael F Peffley
(74) *Attorney, Agent, or Firm* — Wilson Sonsini Goodrich and Rosati, P.C.

(57) ABSTRACT

Systems, devices, and methods to treat a urinary bladder are disclosed. An expandable member is introduced and expanded in the urinary bladder to appose one or more elongate conductors on the outer surface of the expandable member against the inner wall of the urinary bladder. The one or more elongate conductors are used to create a predetermined pattern of electrically isolated tissue regions having reduced electrical propagation such that electrical propagation through the urinary bladder as a whole is reduced. A mucus layer may be removed from the inner bladder wall prior to the ablation. Ablation may be regulated by impedance measurement with the one or more elongate conductors. The urinary bladder may be filled with a fluid to facilitate the impedance measurement.

35 Claims, 16 Drawing Sheets

Related U.S. Application Data is a continuation-in-part of application No. PCT/IB2013/001203, filed on Apr. 19, 2013.

(60) Provisional application No. 61/972,441, filed on Mar. 31, 2014, provisional application No. 61/636,686, filed on Apr. 22, 2012, provisional application No. 61/649,334, filed on May 20, 2012, provisional application No. 62/174,296, filed on Jun. 11, 2015, provisional application No. 61/908,748, filed on Nov. 26, 2013.

(51) Int. Cl.
| | |
|---|---|
| *A61N 1/32* | (2006.01) |
| *A61B 1/307* | (2006.01) |
| *A61B 18/00* | (2006.01) |
| *A61B 18/04* | (2006.01) |
| *A61B 18/18* | (2006.01) |
| *A61B 18/02* | (2006.01) |

(52) U.S. Cl.
CPC ........ *A61N 1/32* (2013.01); *A61B 2018/0016* (2013.01); *A61B 2018/0022* (2013.01); *A61B 2018/00214* (2013.01); *A61B 2018/00488* (2013.01); *A61B 2018/00494* (2013.01); *A61B 2018/00511* (2013.01); *A61B 2018/00517* (2013.01); *A61B 2018/00541* (2013.01); *A61B 2018/00559* (2013.01); *A61B 2018/00577* (2013.01); *A61B 2018/00875* (2013.01); *A61B 2018/00982* (2013.01); *A61B 2018/0212* (2013.01); *A61B 2018/046* (2013.01); *A61B 2018/144* (2013.01); *A61B 2018/1465* (2013.01); *A61B 2018/1861* (2013.01); *A61M 2210/1085* (2013.01)

(58) Field of Classification Search
CPC ........... A61B 2018/00488; A61B 2018/00494; A61B 2018/00511; A61B 2018/00517; A61B 2018/00541; A61B 2018/00559; A61B 2018/00577; A61B 2018/00875; A61B 2018/00982; A61B 2018/0212; A61B 2018/046; A61B 2018/144; A61B 2018/1465; A61B 1/307; A61M 2210/1085; A61N 1/32
See application file for complete search history.

(56) References Cited

U.S. PATENT DOCUMENTS

| | | |
|---|---|---|
| 5,057,106 A | 10/1991 | Kasevich et al. |
| 5,105,360 A | 4/1992 | Akiyama |
| 5,150,717 A | 9/1992 | Rosen et al. |
| 5,178,618 A | 1/1993 | Kandarpa |
| 5,188,602 A | 2/1993 | Nichols |
| 5,209,749 A | 5/1993 | Buelna |
| 5,380,319 A | 1/1995 | Saito et al. |
| 5,405,346 A | 4/1995 | Grundy et al. |
| 5,470,352 A | 11/1995 | Rappaport |
| 5,480,417 A | 1/1996 | Hascoet et al. |
| 5,509,929 A | 4/1996 | Hascoet et al. |
| 5,578,008 A | 11/1996 | Hara |
| 5,599,294 A | 2/1997 | Edwards et al. |
| 5,628,746 A | 5/1997 | Clayman |
| 5,649,973 A | 7/1997 | Tierney et al. |
| 5,769,880 A * | 6/1998 | Truckai ............... A61B 18/1485 607/101 |
| 5,800,486 A | 9/1998 | Thome et al. |
| 5,827,273 A | 10/1998 | Edwards |
| 5,860,951 A | 1/1999 | Eggers et al. |
| 5,902,251 A | 5/1999 | Vanhooydonk |
| 5,967,984 A | 10/1999 | Chu et al. |
| 5,989,284 A | 11/1999 | Laufer |
| 5,992,419 A | 11/1999 | Sterzer et al. |
| 6,001,093 A | 12/1999 | Swanson et al. |
| 6,024,743 A | 2/2000 | Edwards |
| 6,036,689 A | 3/2000 | Tu et al. |
| 6,053,937 A | 4/2000 | Edwards et al. |
| 6,083,255 A | 7/2000 | Laufer et al. |
| 6,097,985 A | 8/2000 | Kasevich et al. |
| 6,161,049 A | 12/2000 | Rudie et al. |
| 6,223,085 B1 | 4/2001 | Dann et al. |
| 6,254,598 B1 | 7/2001 | Edwards et al. |
| 6,283,989 B1 | 9/2001 | Laufer et al. |
| 6,353,751 B1 | 3/2002 | Swanson et al. |
| 6,458,098 B1 | 10/2002 | Kanesaka |
| 6,496,737 B2 | 12/2002 | Rudie et al. |
| RE38,229 E | 8/2003 | Marfurt et al. |
| 6,629,535 B2 | 10/2003 | Ingle et al. |
| 6,692,490 B1 | 2/2004 | Edwards |
| 6,740,108 B1 | 5/2004 | Just et al. |
| 6,875,209 B2 | 4/2005 | Zvuloni et al. |
| 6,997,924 B2 | 2/2006 | Schwartz et al. |
| 7,001,378 B2 | 2/2006 | Yon et al. |
| 7,022,120 B2 | 4/2006 | Lafontaine |
| 7,060,062 B2 | 6/2006 | Joye et al. |
| 7,074,233 B1 | 7/2006 | Gowda et al. |
| 7,081,112 B2 | 7/2006 | Joye et al. |
| 7,083,614 B2 | 8/2006 | Fjield et al. |
| 7,101,368 B2 | 9/2006 | Lafontaine |
| 7,101,387 B2 | 9/2006 | Garabedian et al. |
| 7,192,438 B2 | 3/2007 | Margolis |
| 7,195,625 B2 | 3/2007 | Lentz |
| 7,220,257 B1 | 5/2007 | Lafontaine |
| 7,278,991 B2 | 10/2007 | Morris et al. |
| 7,278,994 B2 | 10/2007 | Goble |
| 7,288,087 B2 | 10/2007 | Winston et al. |
| 7,288,089 B2 | 10/2007 | Yon et al. |
| 7,300,433 B2 | 11/2007 | Lane et al. |
| 7,326,235 B2 | 2/2008 | Edwards |
| 7,357,796 B2 | 4/2008 | Farr et al. |
| 7,371,231 B2 | 5/2008 | Rioux et al. |
| 7,381,208 B2 | 6/2008 | Van Der et al. |
| 7,410,486 B2 | 8/2008 | Fuimanono et al. |
| 7,500,973 B2 | 3/2009 | Vancelette et al. |
| 7,507,234 B2 | 3/2009 | Utley et al. |
| 7,527,622 B2 | 5/2009 | Lane et al. |
| 7,556,628 B2 | 7/2009 | Utley et al. |
| 7,625,368 B2 | 12/2009 | Schechter et al. |
| 7,632,268 B2 | 12/2009 | Edwards et al. |
| 7,648,497 B2 | 1/2010 | Lane et al. |
| 7,655,005 B2 | 2/2010 | Bhola |
| 7,655,006 B2 | 2/2010 | Sauvageau et al. |
| 7,744,594 B2 | 6/2010 | Yamazaki et al. |
| 7,761,169 B2 | 7/2010 | Zelickson et al. |
| 7,813,313 B2 | 10/2010 | Pan et al. |
| 7,837,720 B2 | 11/2010 | Mon |
| 7,846,153 B2 | 12/2010 | Hebert et al. |
| 7,850,681 B2 | 12/2010 | Lafontaine |
| 7,892,229 B2 | 2/2011 | Shadduk et al. |
| 8,007,496 B2 | 8/2011 | Rioux et al. |
| 8,137,342 B2 | 3/2012 | Crossman |
| 8,500,728 B2 * | 8/2013 | Newton ............ A61B 18/1445 606/34 |
| 8,685,050 B2 | 4/2014 | Schur et al. |
| 9,179,963 B2 | 11/2015 | Ben-Ezra et al. |
| 9,327,117 B2 | 5/2016 | Denison et al. |
| 2001/0014805 A1 | 8/2001 | Burbank et al. |
| 2002/0183735 A1 | 12/2002 | Edwards et al. |
| 2003/0055470 A1 | 3/2003 | Mon et al. |
| 2003/0060762 A1 | 3/2003 | Zvuloni et al. |
| 2003/0060813 A1 | 3/2003 | Loeb et al. |
| 2003/0069619 A1 | 4/2003 | Fenn et al. |
| 2003/0178032 A1 | 9/2003 | Ingle et al. |
| 2004/0133254 A1 | 7/2004 | Sterzer et al. |
| 2004/0147915 A1 | 7/2004 | Hasebe |
| 2004/0172112 A1 | 9/2004 | Cioanta et al. |
| 2004/0186468 A1 | 9/2004 | Edwards |
| 2004/0243199 A1 | 12/2004 | Mon et al. |
| 2005/0096647 A1 | 5/2005 | Steinke et al. |

(56) References Cited

U.S. PATENT DOCUMENTS

| | | |
|---|---|---|
| 2005/0107783 A1 | 5/2005 | Tom et al. |
| 2005/0124843 A1 | 6/2005 | Singh |
| 2005/0131500 A1 | 6/2005 | Zalesky et al. |
| 2005/0165389 A1 | 7/2005 | Swain et al. |
| 2005/0228370 A1 | 10/2005 | Sterzer et al. |
| 2005/0251125 A1 | 11/2005 | Pless et al. |
| 2006/0009758 A1 | 1/2006 | Edwards et al. |
| 2006/0118127 A1 | 6/2006 | Chinn |
| 2006/0167442 A1 | 7/2006 | Hebert et al. |
| 2006/0253113 A1 | 11/2006 | Arnold et al. |
| 2006/0253178 A1 | 11/2006 | Masotti |
| 2006/0259029 A1 | 11/2006 | Utley et al. |
| 2007/0005050 A1 | 1/2007 | Duong et al. |
| 2007/0038203 A1 | 2/2007 | Mcintyre |
| 2007/0049918 A1 | 3/2007 | Van Der et al. |
| 2007/0066973 A1 | 3/2007 | Stern et al. |
| 2007/0078451 A1 | 4/2007 | Arnold et al. |
| 2007/0088247 A1 | 4/2007 | Bliweis et al. |
| 2007/0129725 A1 | 6/2007 | Houser |
| 2007/0282184 A1 | 12/2007 | Roberts |
| 2007/0293854 A1 | 12/2007 | Pless et al. |
| 2008/0004613 A1 | 1/2008 | Barbut et al. |
| 2008/0077174 A1 | 3/2008 | Mische |
| 2008/0097427 A1 | 4/2008 | Stern et al. |
| 2008/0125765 A1 | 5/2008 | Berenshyteyn et al. |
| 2008/0140067 A1 | 6/2008 | Vetter et al. |
| 2008/0140070 A1 | 6/2008 | Filloux et al. |
| 2008/0172050 A1 | 7/2008 | Satake |
| 2008/0223380 A1 | 9/2008 | Chinn |
| 2008/0249518 A1 | 10/2008 | Warnking et al. |
| 2008/0262489 A1 | 10/2008 | Steinke |
| 2008/0312642 A1 | 12/2008 | Kania et al. |
| 2009/0018533 A1 | 1/2009 | Perkins et al. |
| 2009/0076494 A1 | 3/2009 | Azure |
| 2009/0131928 A1 | 5/2009 | Edwards et al. |
| 2009/0163906 A1 | 6/2009 | Faure |
| 2009/0248012 A1 | 10/2009 | Maor et al. |
| 2009/0281532 A1 | 11/2009 | Reddy |
| 2009/0306644 A1 | 12/2009 | Mayse et al. |
| 2009/0318914 A1 | 12/2009 | Utley et al. |
| 2010/0004650 A1 | 1/2010 | Ormsby et al. |
| 2010/0030204 A1 | 2/2010 | Stein et al. |
| 2010/0049031 A1 | 2/2010 | Fruland et al. |
| 2010/0049182 A1 | 2/2010 | Ryan et al. |
| 2010/0049186 A1 | 2/2010 | Ingle et al. |
| 2010/0049192 A1 | 2/2010 | Holtz et al. |
| 2010/0076402 A1 | 3/2010 | Mazzone et al. |
| 2010/0076425 A1 | 3/2010 | Carroux |
| 2010/0114087 A1* | 5/2010 | Edwards .................. A61B 8/12 606/33 |
| 2010/0160906 A1 | 6/2010 | Jarrard |
| 2010/0168734 A1 | 7/2010 | Dicarlo |
| 2010/0179530 A1 | 7/2010 | Long et al. |
| 2010/0198066 A1 | 8/2010 | Voegele |
| 2010/0234840 A1 | 9/2010 | Jackson et al. |
| 2010/0262140 A1 | 10/2010 | Watson et al. |
| 2010/0280510 A1 | 11/2010 | Smith et al. |
| 2010/0286688 A1 | 11/2010 | Hughett et al. |
| 2010/0286753 A1 | 11/2010 | Zelickson et al. |
| 2010/0305562 A1 | 12/2010 | Winkler et al. |
| 2011/0028886 A1 | 2/2011 | Mon |
| 2011/0034976 A1 | 2/2011 | Mon et al. |
| 2011/0082450 A1 | 4/2011 | Melsky et al. |
| 2011/0098694 A1 | 4/2011 | Long |
| 2011/0112432 A1 | 5/2011 | Toth |
| 2011/0118719 A1 | 5/2011 | Vissy et al. |
| 2011/0152839 A1 | 6/2011 | Cima et al. |
| 2011/0152855 A1 | 6/2011 | Mayse et al. |
| 2011/0166570 A1 | 7/2011 | Hawkins et al. |
| 2011/0257647 A1 | 10/2011 | Mayse et al. |
| 2011/0264085 A1 | 10/2011 | Satake |
| 2011/0264086 A1 | 10/2011 | Ingle |
| 2011/0301662 A1 | 12/2011 | Bar-Yoseph et al. |
| 2011/0319880 A1 | 12/2011 | Prakash et al. |
| 2012/0004654 A1 | 1/2012 | Jackson et al. |
| 2012/0004656 A1 | 1/2012 | Jackson et al. |
| 2012/0016358 A1 | 1/2012 | Mayse et al. |
| 2012/0022520 A1 | 1/2012 | Bek |
| 2012/0029500 A1 | 2/2012 | Jenson |
| 2012/0059368 A1 | 3/2012 | Takaoka et al. |
| 2012/0065636 A1 | 3/2012 | Thompson et al. |
| 2012/0071870 A1 | 3/2012 | Salahieh et al. |
| 2012/0071873 A1 | 3/2012 | Thompson et al. |
| 2012/0101490 A1 | 4/2012 | Smith |
| 2012/0116384 A1 | 5/2012 | Truckai |
| 2012/0130363 A1 | 5/2012 | Kim et al. |
| 2012/0143179 A1 | 6/2012 | Avitall |
| 2013/0018281 A1 | 1/2013 | Nagale et al. |
| 2013/0066308 A1 | 3/2013 | Landman |
| 2013/0090648 A1* | 4/2013 | Nagale .................. A61B 5/6852 606/41 |
| 2013/0158536 A1 | 6/2013 | Bloom et al. |
| 2013/0177505 A1 | 7/2013 | Somerville et al. |
| 2014/0081257 A1* | 3/2014 | Ghoniem ........... A61B 18/1477 606/33 |
| 2014/0148798 A1* | 5/2014 | Sachs .................. A61B 18/1485 606/33 |
| 2014/0324036 A1 | 10/2014 | Sachs et al. |
| 2015/0142074 A1 | 5/2015 | Bar-Yoseph et al. |
| 2015/0157389 A1 | 6/2015 | Ben-Ezra et al. |
| 2015/0157391 A1 | 6/2015 | Ben-Ezra et al. |
| 2015/0164401 A1* | 6/2015 | Toth .................. A61B 5/04882 600/301 |
| 2016/0030107 A1 | 2/2016 | Herbst et al. |
| 2016/0120598 A1* | 5/2016 | Brink .................. A61B 5/1107 606/34 |

FOREIGN PATENT DOCUMENTS

| | | |
|---|---|---|
| WO | WO-2013016588 A1 | 1/2013 |
| WO | WO 2013/052848 A1 | 4/2013 |
| WO | WO 2013/052852 A1 | 4/2013 |
| WO | WO 2013/160772 A2 | 10/2013 |

OTHER PUBLICATIONS

Gibbon, et al., Transection of the bladder for adult enuresis and allied conditions. British Journal of Urology. 1973; 45: 306-309.

Hasan, et al., Outcome of endoscopic bladder transection. British Journal of Urology. 1995; 75: 592-596.

Hindmarsh, et al., Bladder transection for adult enuresis. British Journal of Urology. 1977; 49: 515-521.

International Search Report dated Mar. 15, 2017 for International Application No. PCT/IB2016/000953.

Kumar, S.P. and Abrams, P.H. Detrusor myectomy: long-term results with a minimum follow-up of 2 years. British Journal of Urology International. Aug. 2005; 96(3): 341-44.

Lucas, M.G. and Thomas, D.G. Endoscopic bladder transection for detrusor instability. British Journal of Urology. 1987; 59: 526-528.

Mahony, D. T. and Laferte, R. O. Studies of enuresis. IV. Multiple detrusor myotomy: a new operation for the rehabilitation of severe detrusor hypertrophy and hypercontractility. Journal of Urology. 1972; 107: 1064-1067.

Mammen, et al., Robotic Transperitoneal Detrusor Myotomy: Description of a Novel Technique. Journal of Endourology. May 2005; 19(4).

Mundy, A.R. Long-term results of bladder transection for urge incontinence. British Journal of Urology. 1983; 55: 542-642.

Office Action dated Apr. 28, 2017 for U.S. Appl. No. 14/519,933.

Office Action dated Dec. 13, 2016 for U.S. Appl. No. 14/519,933.

Parsons, et al., Endoscopic bladder transection. British Journal of Urology. 1984; 56 : 625-628.

Potter, et al., Detrusor myotomy: a 5-year review in unstable and non-compliant bladders. British Journal of Urology International. 2002; 89: 932-935.

Staskin, et al., Bladder Transection—a Functional, Neurophysiological, Neuropharmacological and Neuroanatomical Study. British Journal of Urology. 1981; 53: 552-557.

Swami, et al., Detrusor myectomy for detrusor overactivity: a minimum 1-year follow-up. British Journal of Urology. Jan. 1998; 81(1):68-72.

(56) References Cited

OTHER PUBLICATIONS

Turner-Warwick, R. T. and Ashken, M. H. The functional results of partial, subtotal and total cystoplasty with special reference to ureterocystoplasty, selective sphincterotomy and cystocystoplasty. British Journal of Urology. 1967; 39: 3-12.
Yazan, et al., The outcome of detrusor myotomy in children with neurogenic bladder dysfunction. The Journal of Urology. Jun. 2004; 171: 2654-2656.
Zuban, et al., Surgical correction of overactive bladder resistant to standard therapy. (In Russian) Jul.-Aug. 2010; 4:11-15.
Notice of Allowance dated Sep. 26, 2017 for U.S. Appl. No. 14/519,933.
Notice of Allowance dated Oct. 17, 2017 for U.S. Appl. No. 14/519,933.
U.S. Appl. No. 14/519,933, filed Oct. 21, 2014.
U.S. Appl. No. 14/602,493, filed Jan. 22, 2015.
Banakhar, et al. Pathophysiology of overactive bladder. Int Urogynecol J. Aug. 2012;23(8):975-82. doi: 10.1007/s00192-012-1682-6. Epub Feb. 7, 2012.
Biers, et al. The functional effects of a c-kit tyrosine inhibitor on guinea-pig and human detrusor. BJU Int. Mar. 2006;97(3):612-6.
Brading. A myogenic basis for the overactive bladder. Urology. Dec. 1997;50(6A Suppl):57-67; discussion 68-73. Review.
Brading. Overactive bladder: Why it occurs. Women's Health Medicine 2.6 (2005): 20-23.
Cruz, et al. Bladder wall thickness in overactive bladder: does it have a role?. European Urology Supplements 8.9 (2009): 769-771.
Drake, et al. Localized contractions in the normal human bladder and in urinary urgency. BJU Int. May 2005;95(7):1002-5.
Elbadawi, et al. Structural basis of geriatric voiding dysfunction. VI. Validation and update of diagnostic criteria in 71 detrusor biopsies. J Urol. May 1997;157(5):1802-13.
European search report and opinion dated Nov. 13, 2015 for EP Application No. 13781035.4.
Fry, et al. Spontaneous activity and electrical coupling in human detrusor smooth muscle: implications for detrusor overactivity? Urology. Mar. 2004;63(3 Suppl 1):3-10.
Haferkamp, et al. Structural basis of neurogenic bladder dysfunction. II. Myogenic basis of detrusor hyperreflexia. J Urol. Feb. 2003;169(2):547-54.
Hammad. Electrical propagation in the renal pelvis, ureter and bladder. Acta Physiol (Oxf). Feb. 2015;213(2):371-83. doi: 10.1111/apha.12392. Epub Sep. 30, 2014. Review.
Ikeda, et al. Urotheliogenic modulation of intrinsic activity in spinal cord-transected rat bladders: role of mucosal muscarinic receptors. Am J Physiol Renal Physiol. Aug. 2008;295(2):F454-61. doi: 10.1152/ajprenal.90315.2008. Epub Jun. 11, 2008.
International search report and written opinion dated Jan. 24, 2014 for PCT Application No. IB2013/001203.
International search report and written opinion dated Aug. 12, 2015 for PCT Application No. IB2014/003083.
Kanai, et al. Origin of spontaneous activity in neonatal and adult rat bladders and its enhancement by stretch and muscarinic agonists. Am J Physiol Renal Physiol. Mar. 2007;292(3):F1065-72. Epub Nov. 14, 2006.
Lentle, et al. Characterisation of the contractile dynamics of the resting ex vivo urinary bladder of the pig. BJU Int. Dec. 2015;116(6):973-83. doi: 10.1111/bju.13132. Epub Jun. 13, 2015.
McCloskey. Interstitial cells in the urinary bladder—localization and function Neurourol Urodyn. 2010;29(1):82-7. doi: 10.1002/nau.20739. Review.
Notice of allowance dated Sep. 16, 2015 for U.S. Appl. No. 14/602,493.
Office action dated Jun. 19, 2015 for U.S. Appl. No. 14/602,493.
Parsons, et al. A Further Assessment of Bladder Transection in the Management of Adult Enuresis and Allied Conditions. Br J Urol. Nov. 1977;49(6):509-14.

\* cited by examiner

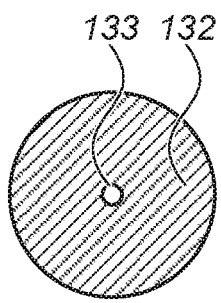
FIG. 13A
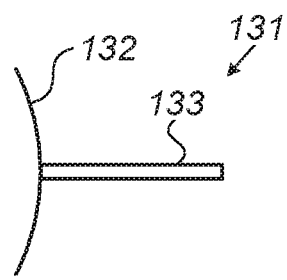
FIG. 13B
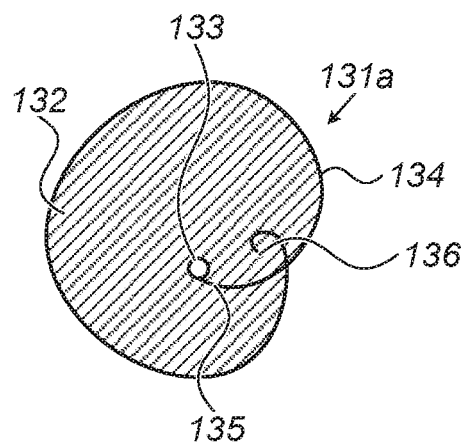
FIG. 13C
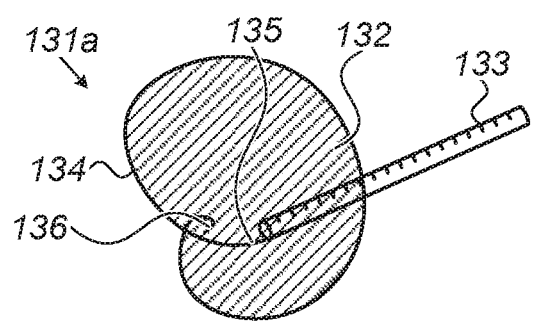
FIG. 13D
FIG. 14A
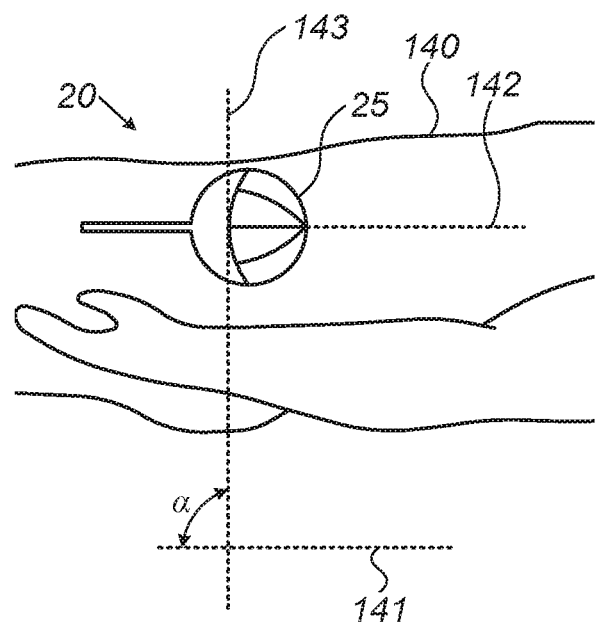

DEVICES AND METHODS FOR TRANSURETHRAL BLADDER PARTITIONING

CROSS-REFERENCE

This application claims the benefit of U.S. Provisional Application No. 62/174,296, filed Jun. 11, 2015; and, this application is a continuation-in-part of U.S. patent application Ser. No. 14/519,933, filed Oct. 21, 2014, now U.S. Pat. No. 9,883,906, which claims priority to U.S. Provisional Patent Application Nos. 61/908,748, filed Nov. 26, 2013, and 61/972,441, filed Mar. 31, 2014; and application Ser. No. 14/519,933 is also a continuation-in-part of PCT Application No. PCT/IB2013/001203, filed Apr. 19, 2013, which claims priority to U.S. Provisional Patent Application Ser. Nos. 61/636,686, filed Apr. 22, 2012, and 61/649,334, filed May 20, 2012; all of which are incorporated herein by reference in their entirety.

BACKGROUND

The present disclosure relates to systems, devices, and methods to treat a bodily organ and disorders thereof. In particular, the present disclosure describes improved devices and methods for treating a urinary bladder or other bodily organ by partitioning the organ into electrically isolated zones according to a predetermined pattern.

A. The Normal Bladder.

1. Structure:

The urinary bladder is located in the pelvic cavity anterior to the rectum and superior to the reproductive organs of the pelvis. In females, the urinary bladder is somewhat smaller in size compared to males and must share the limited space of the pelvic cavity with the uterus that rests superior and posterior to it.

The urinary bladder functions as a storage vessel for urine, to delay the frequency of urination. It is one of the most elastic organs of the body and is able to increase its volume greatly to accommodate between 600 to 800 ml of urine at maximum capacity.

The bladder wall is made of three distinct layers:

(1) The mucosa (adjacent to the bladder lumen) comprising the transitional epithelium of the bladder (Urothelium) and the underlying lamina propria.

(a) The transitional epithelium with its typical tight junctions, make an impermeable layer, effectively separating the urine from the body. The lamina proporia layer is rich with blood vessels (forming the sub mucosal plexus) and nerve endings, to support the Urothelium. Interstitial Cells of Cagal (a.k.a ICC or myofibroblasts) in the lamina propria form a network of excitable cells, with "nerve like" electrical conduction properties, and intrinsic "pacemaker" qualities (detailed below). Microscopic studies, augmented by immunochemical staining, show these cells are in intimate contact with the nerve ending of the lamina propria, mediating transmission of membrane potential transients from the nerves and the Urothelium to the detrusor.

(b) In addition, the mucosa has important paracrine activities, secreting various growth hormones and cytokines that affect adjacent cells and the underlying detrusor. (Kanai et al., *Origin of spontaneous activity in neonatal and adult rat bladders and its enhancement by stretch and muscarinic agonists, Am J Physiol Renal Physiol* 292: F1065-F1072, 2007)

(c) Blood vessel plexuses underlie the urothelium (sub endothelial plexus), and the mucosa (submucosal plexus), forming functional anastomoses between adjacent wall areas, important for the paracrine activities of the bladder.

(2) The muscularis—the middle layer, contains the bulk of the bladder muscle. The muscularis is commonly referred to as the detrusor muscle and contracts during urination to expel urine from the body. Also, the muscularis is rich with ICC cells, arranged along the muscle bundles, forming smaller, more local networks. (McClosekey K D, *Interstitial Cells in the Urinary Bladder—Localization ad Function, Neurourology and Urodynamics* 29:82-87 (2010))

(3) The adventitia—a connective tissue layer encompassing the bladder, containing the larger blood vessels and nerves of the bladder. Although able to stretch and contract, the adventitia is limited in its elasticity, probably limiting the expansion of other layers, thus protecting the bladder from over expansion. Most blood vessels and nerves enter the adventitia at the bladder neck, and are thus oriented along the longitudinal axis of the bladder, when it is full.

The lower urinary tract is innervated by a complex neural network including sympathetic innervation, parasympathetic innervation, and somatic innervation. The majority of bladder nerves are efferent, however, extensive afferent innervation (mostly unmyelinated C-fibers) carries information from the bladder to the central nervous system. Some of the afferent traffic becomes conscious (bladder sensations), and some terminates at lower CNS levels, as part of the spinal reflexes involved in bladder control.

2. Function a) Filling Phase

Except for brief micturition episodes, the bladder is constantly filling. In the filling phase, the bladder is in a high compliance state, accumulating urine at changing rates, greatly increasing in volume (~tenfold), while maintaining a low intraluminal pressure, critical to allow draining from the low pressure renal collecting system.

Grossly, the parasympathetic innervation increases bladder tone and facilitates bladder contraction. The sympathetic autonomic innervation decreases bladder tone, and facilitates bladder relaxation. The cerebral control is predominately inhibitory to bladder contraction, and is normally only temporarily withheld during micturition, to facilitate bladder contraction.

The filling phase is characterized by rhythmic contractile activity of the bladder, producing gentle periodic fluctuations in intraluminal bladder pressure. This periodic activity is pivotal in maintenance of bladder tone and accommodation to changing pressures (luminal as well as external). These contractions are not dependent on external innervation, and persist also in ex-vivo (denervated) bladders, persist in the presence of chemical neural blocks (such as tetrodotoxin), and are seen even in isolated bladder strips.

Interstitial Cells of Cagal (ICC) throughout the bladder, and especially in the Urothelium—Lamina Propria junction, act as pacemakers, initiating these activities. Recently, it has been shown that electrical activity originating in these pacemaker sites propagates through the bladder wall, creating propagating patches of contraction (PPC), important in maintaining bladder shape and pressure. (Chambers et al., *Characterisation of the contractile dynamics of the resting ex vivo urinary bladder of the pig, BJU Int* 2015 116:973-983.) These PPC's are most frequent on the anterior and superior aspects of the bladder, and less frequent on the posterior aspect of the bladder, and are almost never seen to cross the trigone area. Typically, large PPC may cover up to one fifth of the bladder area.

To note, electrical propagation through the normal detrusor is minimal, mostly limited to individual myocyte bundles. The electrical coupling between normal detrusor muscle cells is poor, and current injected into the detrusor barely travels more than 0.3 mm, in the axial direction, and even less (if at all) transverse to the bladder axis. (Hammad F T, *Electrical propagation in the renal pelvis, ureter and bladder, Acta Physiol* 2015 213:371-383.) This is substantially different in overactive bladders, as will be detailed below.

b) Micturition

Normal micturition is characterized by voluntary initiation of timely expulsion of urine, with complete emptying the bladder. Since the detrusor muscle itself cannot be consciously contracted, conscious control of voiding is mediated by reflexes originating in the bladder neck, where somatic innervation allows voluntary relaxation of the internal sphincter and bladder neck. Once the bladder neck is relaxed (and thus stretched), coordinated bladder contraction takes place, with almost simultaneous contraction of the entire detrusor, for an average of approx. 20 seconds (average micturition duration). Such rapid coordination of almost simultaneous detrusor contraction during micturition is carried out by the nervous networks (mostly parasympathetic), and not by the relatively slow ICC network.

Normally, the resistance of the lower urinary tract is low, and modest pressures (up to 40 cmH2O) are sufficient for timely urine expulsion. Once the bladder completely empties (residual volumes in the range of up to 30 cc are considered normal), gradual bladder relaxation occurs, with return to the low pressures of the filling phase within minutes.

B. Overactive Bladder (OAB).

1. Causes

Overactive bladder is a disorder of the bladder filling phase. While micturition function is usually preserved, the filling phase exhibits pathological contractile activity, disturbing bladder filling with a sudden, premature urge to urinate.

It is hypothesized that malfunction of any of the normal bladder functions can lead to overactive bladder symptoms. For example "Neurogenic OAB" develops after a stroke, or spinal cord injury, resulting with loss of cerebral inhibition, inducing bladder overactivity. OAB symptoms may also develop in response to bladder outlet obstruction, so called "Obstructive OAB". In these cases, bladder outlet obstruction by prostatic hypertrophy or pelvic organ prolapse, results with bladder wall myocyte hypertrophy and overactivity. However, in most cases, the reason for OAB remains unknown, and is classified as "idiopathic OAB".

2. Pathophysiology of OAB

In most cases, there is no obvious pathology that explains the bladder overactivity. Some experts believe the symptoms of OAB reflect normal aging. Some believe that local bladder wall ischemia (in response to bladder hypertrophy and/or micro-vessel arthrosclerosis) is the reason for increased bladder sensations and overactivity. Others attribute the overactivity to local factors, including increased levels of growth hormones and cytokines that act locally (paracrine activity) causing changes in the myocyte function. However, whatever the exact cause, several important observations are commonly seen in OAB, pointing at a common end result that might have different origins in different cases. (Banakhar 2012. *Pathophysiology of overactive bladder.*) (Brading 2005. *Overactive bladder why it occurs.*)

Macroscopic changes—On average, overactive bladders have a thicker wall than normally functioning bladders. This is especially pronounced in longstanding neurogenic bladders, and bladders with an obstructed outlet. Although overactive and/or obstructed bladders are usually thicker walled than normal controls, much overlap is reported, and the variability between people (as well as in between studies) is large. (Cruz et al. *EUROPEAN UROLOGY SUPPLEMENTS* 8 (2009) 769-771).) Wall thickness is increased on average by ~20%, however overactive bladder is quite common also in bladders with normal wall thickness, and increased wall thickness is quite common in normally functioning bladders.

Microscopic changes—Electron microscopy of overactive bladders show alien muscle cell junctions (protrusion junctions or ultra-close abutments) with narrow gaps that mediate abnormal electrical cell coupling. Chain-like linkage of several detrusor muscle cells by such junctions are reported to create erratic irritable foci that readily activate the final common pathway. These changes were reported in overactive bladders of different species, with different underlying causes, and are absent in stable detrusors. (Haferkamp 2003. *Structural basis of neurogenic bladder dysfunction. II. Myogenic basis of detrusor hyperreflexia.*) (Elbadawi 1997. *Structural basis of geriatric voiding dysfunction. VI. Validation and update of diagnostic criteria in 71 detrusor biopsies.*) Another microscopic finding seen using light microscopy, is an increased number of ICC cells in overactive bladders. These too, act for increased electrical interconnectivity in overactive bladders.

Contractile behavior—overactive bladders are often characterized by tetanic contractions, of high amplitude, at low bladder volumes. These contractions are symptomatic, and regional, at least initially. Such contractions have been demonstrated in entire bladders, as well as in isolated bladder strips, and even in human biopsy samples. (Drake 2004. *Localized contractions in the normal human bladder and in urinary urgency.*) (Brading 1997. *A myogenic basis for the overactive bladder.*)

Increased pacemaker activity and electrical conduction—overactive bladders develop much larger, but less frequent, spontaneous bladder contractions, and intra vesical pressure changes. These enhanced contractions are associated with fewer pacemaker sites that propagate more rapidly and over larger portions of the bladder. (Ikeda 2008. *Urotheliogenic modulation of intrinsic activity in spinal cord-transected rat bladders.*) (Fry 2004. *Spontaneous activity and electrical coupling in human detrusor smooth muscle implications for detrusor overactivity.*) In an animal model of neurogenic OAB, PPCs travel the surface of the bladder in various routes, covering approximately a fifth of the bladder surface before spontaneously terminating. Often propagation is circular and re-entrant, much like in cardiac arrhythmia. PPCs exist also in normal bladders, however, their magnitude markedly increases in overactive bladders. (Chambers et al., *Characterisation of the contractile dynamics of the resting ex vivo urinary bladder of the pig, BJU Int* 2015 116:973-983.)

The crucial role of such electrical connectivity was experimentally demonstrated by a c-kit tyrosine inhibitor that specifically targets ICC cells. When the ICC network was disabled by such an agent, human strips of overactive bladders ceased to exhibit exaggerated responses to carbachol, effectively exhibiting return to normal (control) behavior once the ICC network was disabled. (Biers S M., *The functional effects of a c-kit tyrosine inhibitor on guinea pig and human detrusor, BJU International* 97:612-616 (2005).)

Thus, the exact reason of OAB is yet unknown and probably more than one condition can cause OAB. While neural autonomic control is crucial for normal micturition and normal inhibition of bladder tone during the filling phase, bladder activity in the filling phase is mostly of myogenic origin, persisting independently of neural control. Over-activity is manifested by uninhibited, generalized tetanic bladder contractions in the filling phase. Such contractions are initiated by independent local pacemakers and propagate through the bladder wall via pathologically increased electrical conduction.

Current pharmaceutical OAB treatments offer only temporary and partial relief for the problem. The only permanent solutions currently available are surgical, and carry significant morbidity. Currently available therapies aim at modulating the activity of the nerves governing bladder function, either by electrical stimulation, by interference with synaptic communication, or by physical disruption of the nerves. While this approach has proven effect, efficacy is limited, and clinically significant OAB remains severely symptomatic in the vast majority of cases.

For at least the above reasons, there remains a major need for a novel treatment for OAB that is safe, effective, minimally invasive, and long lasting.

SUMMARY

The approach of the current present disclosure is directed at disrupting the abnormal electrical activity and conduction of the overactive bladder wall. This approach was tried and tested in disruption of abnormal electrical activity and conduction pathways to treat cardiac arrhythmia. The technologies used in these procedures have an excellent clinical track record of long lasting efficacy in the cardiac context (effectively definitive relief in the vast majority of cases), with excellent safety and tolerability.

As with cardiac ablation, TBP may utilize controlled radio frequency (RF) energy, to accurately ablate thin tissue lines, effectively "fencing" abnormal activity (electrical and paracrine) and limiting their spread to the entire organ.

TBP treatment may be applied in a minimally invasive, office based procedure. The treatment system may comprise a disposable, low profile, RF probe (OD<21F) such as device 20 shown in FIG. 2, and an RF generator. Under local anesthesia only, the device 20 may be advanced through urethra 15, to reach the urinary bladder lumen 12. The catheter may then be expanded (up to approximately tenfold its insertion diameter), to appose the bladder wall. RF power from the proprietary generator may be applied through the catheter, creating thin RF ablation lines in the bladder, effectively partitioning the bladder into several electrically independent zones (Hence: Transurethral Bladder Partitioning).

Abnormal electrical activity and conduction within the bladder wall are an established fact in OAB, and the inventors believe that reversing these changes (by ablation lines partitioning the bladder) will reverse the OAB symptoms. Such disruption of conduction was shown in preclinical studies to alleviate OAB (i.e., by the anti-cancer drug Glivec). Furthermore, such disruption was once widely performed surgically (bladder transection, and bladder myotomy), showing outstanding efficacy, albeit significant morbidity.

The present disclosure offers a minimally invasive, safe and easy procedure to parallel the success of these procedures, without resorting to major surgery.

Aspects of the present disclosure provide methods of treating a disorder in a urinary bladder or other hollow bodily organs. A predetermined pattern of electrically isolated tissue regions having reduced electrical propagation may be created in an inner wall of the urinary bladder such that electrical propagation through the urinary bladder as a whole is reduced.

In many embodiments, a mucus layer is removed from an inner wall of the urinary bladder. Removal of the mucus layer may facilitate the creation of the predetermined pattern of electrically isolated tissue regions. To remove the mucus layer, one or more of a high pressure fluid jet, a soap fluid, a solvent fluid, an acidic fluid, an enzymatic fluid, a pharmacological agent, an antiseptic fluid, a detergent, or mechanical remover may be introduced into to the bladder.

In some embodiments, the bladder may be filled with one or more fluids. For example, the bladder may be filled with a cold fluid, a conductive fluid, a non-conductive fluid, or a local anesthetic, to name a few, to facilitate the creation of the predetermined pattern of electrically isolated tissue regions.

In many embodiments, the urinary bladder is visualized such as with a cystoscope prior to creating the predetermined pattern of electrically isolated tissue regions. The positions of ureteral orifices of the urinary bladder may be assessed by the visualization.

To create the predetermined pattern of electrically isolated tissue regions, a tissue modification device may be advanced through the urethra to reach the urinary bladder, an expandable member disposed at the end of the distal end of the tissue modification device may be advanced within the urinary bladder such than an outer surface of the expandable member contacts the inner wall of the urinary bladder, and the inner wall of the urinary bladder may be ablated with at least one elongate conductor positioned at the outer surface of the expandable member contacting the inner wall. The expandable member may be expanded to a size based on a distance between a ureteral orifice and a bladder neck of the urinary bladder.

In some embodiments, it may be determined whether the at least one elongate conductor has contacted the inner wall sufficiently to ablate the inner wall. This determination may be made by measuring an impedance of the inner wall with the at least one elongate conductor, such as a change over time of the impedance. This change over time may comprise one or more of: an initial increase indicating contact between the at least one elongate conductor and the inner wall, a sequential rapid drop which may indicate a breach in an epithelium, a further reduction which may indicate successful tissue modification, and a third reduction which may indicate successful detachment of the at least one elongate conductor from the inner wall. The impedance of the inner wall may be measured with the urinary bladder filled with a conductive fluid. The impedance of the inner wall may be measured with the urinary bladder filled with a non-conductive fluid. In response to the measured impedance or changes thereto, ablation may be reduced or halted. For instance, ablation may be reduced or halted when the measured impedance is changed by a threshold amount. This threshold amount may depend on whether the urinary bladder is filled with a conductive or non-conductive fluid; and, the methods herein may include a step of comprising indicating whether the urinary bladder is filled with a conductive or non-conductive fluid.

In some embodiments, the expandable member may comprise one or more markings denoting electrode positions and the distance therefrom.

In some embodiments, the tissue modification device and the expandable member comprises a lumen configured for insertion of an endoscope there through while the expandable member is expanded.

In some embodiments, one or more non-targeted areas of the inner wall of the urinary bladder, such as the ureteral orifices, may be shielded from ablation.

The predetermined pattern of electrically isolated tissue regions may comprise one or more of at least one circumferential ablation line or at least one longitudinal ablation line in the inner wall of the urinary bladder. The predetermined pattern of electrically isolated tissue regions may comprise one or more of at least one circumferential ablation line and at least one longitudinal ablation line in the inner wall of the urinary bladder. The at least one circumferential ablation line may be inclined in relation to the at least one longitudinal ablation line. The at least one circumferential ablation line may be inclined in relation to the at least one longitudinal ablation line between 15 to 90 degrees. The at least one circumferential ablation line may be anteriorly inclined in relation to a long axis of a body of a patient. The at least one circumferential ablation line may be inclined in relation to the at least one longitudinal ablation line based on a distance between a ureteral orifice and a bladder neck of the urinary bladder. The at least one longitudinal ablation line may be distal to the at least one circumferential line. For example, the ablation pattern may comprise a circumferential ablation line and a plurality of longitudinal ablation lines extending distally (with respect to the urethra, or in the direction from the urethra to the bladder apex) from the circumferential ablation line.

The integrity of the urinary bladder may be verified such as by filling the urinary bladder with a known volume of fluid prior to creating the predetermined pattern of electrically isolated tissue regions, draining the urinary bladder after creating the predetermined pattern of electrically isolated tissue regions, measuring a volume of the drained fluid, and comparing the measured volume with the known volume.

In some embodiments, the predetermined pattern of electrically isolated tissue regions may also have reduced diffusion capacity such that diffusion through the urinary bladder as a whole is reduced.

In some embodiments, the predetermined pattern of electrically isolated tissue regions may limit collateral blood blow across ablation lines of the predetermined pattern such that superficial blood mixing and flow along a plane of the inner wall of the urinary bladder is reduced. Blood flow across the inner wall of the urinary bladder may remain un-disturbed.

In some embodiments, the dimensions of the urinary bladder are measured. The pattern of electrically isolated tissue regions may be predetermined based on the measured dimensions.

In some embodiments, one or more ureteral orifice may be covered as the predetermined pattern of electrically isolated tissue regions is created. The one or more ureteral orifice may be covered with an electrically or thermally insulative shield or plug.

Aspects of the present disclosure also provide systems for treating a urinary bladder. An exemplary system may include a catheter shaft, an expandable member, at least one elongate conductor, and at least one shield. The expandable member may be coupled to a distal end of the catheter shaft and configured to be expanded within the urinary bladder. The at least one elongate conductor may be disposed on an outer surface of the expandable member and may be configured to ablate an inner wall of the urinary bladder when the expandable member is expanded within the urinary bladder. The at least one shield may be disposed on the outer surface of the expandable member to cover at least one ureteral orifice when the expandable member is expanded within the urinary bladder. The at least one shield may be inserted into the urinary bladder separately from the expandable member. The at least one shield may have one or more of a triangular, square, oblong, heart, letter V, letter U, letter C, spiral, elliptical, oval, circular, or oblong shape. The at least one shield may comprise a first shield for covering a first ureteral orifice and a second shield for covering a second ureteral orifice. The at least one shield may be electrically or thermally insulative.

Aspects of the present disclosure also provide systems and methods for minimal invasive diagnosis of a urinary bladder. An exemplary system may comprise an intravesical imaging or sensing apparatus, an extravesical imaging or sensing apparatus, and a processor. Urinary bladder data may be acquired simultaneously from the intravesical and extravesical imaging or sensing apparatuses. Data from both said intravesical and extravesical imaging or sensing apparatuses may be collected by the processor. The processor may eliminate bladder activity caused by extravesical activity, compare net bladder activity to a database of normal activity, and identify aberrant activity patterns.

Aspects of the present disclosure also provide further methods of treating a disorder in a urinary bladder. A predetermined pattern of scar tissue having reduced diffusion capacity may be created in the urinary bladder, and the predetermined pattern may define isolated bladder regions such that diffusion through the bladder as a whole is reduced. Alternatively or in combination, a predetermined pattern of ablation lines may be created through a subendothelial or submucosal plexus but no further in the urinary bladder, and collateral blood flow across said ablation lines may be limited such that superficial blood mixing and flow along a plane of the bladder wall is reduced while blood flow across the bladder wall remains un-disturbed. To create the predetermined pattern, a tissue modification device may be advanced through the urethra to reach the urinary bladder, an expandable member disposed at the end of the distal end of the tissue modification device may be expanded within the urinary bladder such than an outer surface of the expandable member contacts the inner wall of the urinary bladder, and the inner wall of the urinary bladder may be ablated with at least one elongate conductor positioned at the outer surface of the expandable member contacting the inner wall.

Aspects of the present disclosure also provide further devices for treating a disorder in a urinary bladder. An exemplary device may comprise a shaft, an expandable member, and at least one elongate conductor disposed over an outer surface of the expandable member. The shaft may be advancable through a urethra of a patient to reach the urinary bladder. The shaft may have a longitudinal axis. The expandable member may be coupled to a distal end of the shaft. The expandable member may have a collapsed configuration advancable through the bodily passage to reach the cavity of the organ and an expanded configuration configured to contact an inner wall of the urinary bladder when the expandable member is advanced therein. The expandable member in at least the expanded configuration may have a central axis offset from the longitudinal axis of the shaft. The at least one elongate conductor may be configured to contact the inner wall of the urinary bladder when the expandable member is advanced and expanded therein to create a predetermined pattern of one or more ablation lines therein. The central axis of the expandable member may be offset from the longitudinal axis of the shaft at a tilt angle greater than 0 such that the at least one elongate conductor avoids contact with ureteral orifices of the urinary bladder when the shaft is advanced through the urethra and the expandable member is expanded within the urinary bladder. The tilt angle may be between 0 and 90 degrees. The predetermined pattern of the one or more ablation lines may be configured to create tissue regions having reduced electrical propagation in the inner wall of the urinary bladder.

The at least one elongate conductor may comprise at least one longitudinal conductor and at least one latitudinal conductor. The at least a part of the at least one latitudinal conductor may be configured to be parallel to the at least one longitudinal conductor when the expandable member is collapsed and may be substantially parallel to an equator of the expandable member when the expandable member is expanded. The at least one longitudinal conductor may be parallel to a longitudinal axis of the shaft.

In some embodiments, the expandable member is disposed over a distal end of the shaft. The distal end of the shaft may be telescopic to extend in length as the expandable member transitions from the collapsed to the expanded configuration. The telescopic distal end of the shaft may vary in length from 2 cm to 5 cm when collapsed to 4 cm to 15 cm when fully extended. The device may further comprise a hinge coupling the shaft and the expandable member.

Aspects of the present disclosure also provide further systems for treating a disorder in a urinary bladder. An exemplary system may comprise means for creating a predetermined pattern of electrically isolated tissue regions having reduced electrical propagation in an inner wall of the urinary bladder such that electrical propagation through the urinary bladder as a whole is reduced. The predetermined pattern of electrically isolated tissue regions may comprise one or more of at least one circumferential ablation line or at least one longitudinal ablation line in the inner wall of the urinary bladder.

The system may further comprise comprising means for removing a mucus layer from an inner wall of the urinary bladder. Removal of the mucus layer may facilitate the creation of the predetermined pattern of electrically isolated tissue regions. The means for removing the mucus layer may comprise one or more of a high pressure fluid jet, a soap fluid, a solvent fluid, an acidic fluid, an enzymatic fluid, a pharmacological agent, an antiseptic fluid, a detergent, or mechanical remover to the bladder.

The system may further comprise means of filling the bladder with one or more of a conductive fluid, a non-conductive fluid, or a local anesthetic. The system may further comprise means for one or more of visualizing the urinary bladder or assessing positions of ureteral orifices of the urinary bladder. The system may further comprise means for verifying an integrity of the urinary bladder.

The means for creating a predetermined pattern of electrically isolated tissue regions may comprise at least one elongate conductor positioned on an outer surface of an expandable member of a tissue modification device. The system may further comprise means for determining whether the at least one elongate conductor has contacted the inner wall sufficiently to ablate the inner wall, such as means for measuring an impedance of the inner wall.

The system may further comprise means for shielding one or more non-targeted areas of the inner wall of the urinary bladder from ablation as the predetermined pattern of electrically isolated tissue regions is created. The one or more non-targeted areas of the inner wall of the urinary bladder may comprise a ureteral orifice.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 13A is a simplified schematic front view of a ureteral plug, according to many embodiments.

FIG. 13B is a simplified schematic side view of a ureteral plug, according to many embodiments.

FIG. 13C is a simplified schematic front view of a spiral ureteral plug, according to many embodiments.

FIG. 13D is a simplified schematic three-dimensional depiction of a spiral ureteral plug, according to many embodiments.

FIG. 14A is a simplified schematic side view of a TBP device in its deployed and expanded state within a bladder, according to many embodiments.

DETAILED DESCRIPTION

The present disclosure describes improved devices and methods for treating a urinary bladder or other bodily organ by partitioning the organ into electrically isolated zones according to a predetermined pattern. Such methods to treat urinary disorders may be termed transurethral bladder partitioning (TBP) therapy.

In brief, prior applications by the inventors describe treatment of micturition disorders of a urinary bladder by creating in its wall a pattern of electrically isolated zones, according to a predetermined pattern.

A short description of the main elements of these applications follows.

Figure 1:
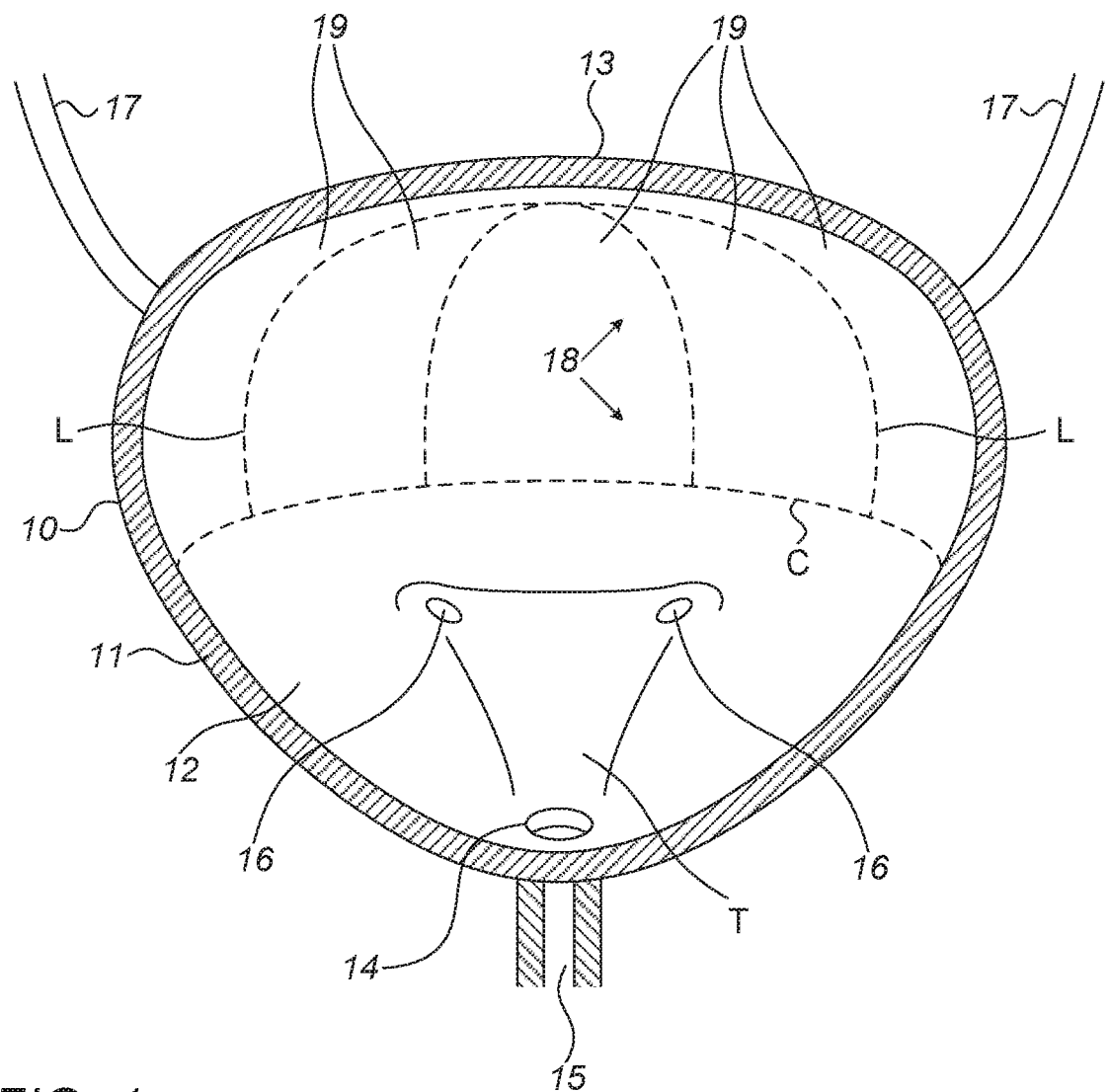
FIG. 1 is a simplified schematic section in the coronal plain, of a urinary bladder showing an ablation pattern, according to many embodiments.

FIG. 1 shows a urinary bladder with such an ablation pattern, which may be produced by the devices described in the prior applications and herein.

More particularly, FIG. 1 is a simplified schematic section in the coronal plain, of a urinary bladder 10, having a wall 11, a lumen 12, an apex 13, an outlet 14, a urethra 15, and two ureteral orifices 16, which are the openings of ureters 17. The triangle connecting bladder outlet 15 and ureteral orifices 16 is the trigone T, which is a highly innervated area of the bladder wall. In the upper hemisphere of bladder 10, is shown ablation pattern 18 within bladder wall 11, which may comprise longitudinal lines L, circumferential lines C, or other lines or shapes in accordance with the invention. Lines L and C of pattern 18 may divide wall 11 of bladder 10 into electrically isolated zones 19.

Figure 2:
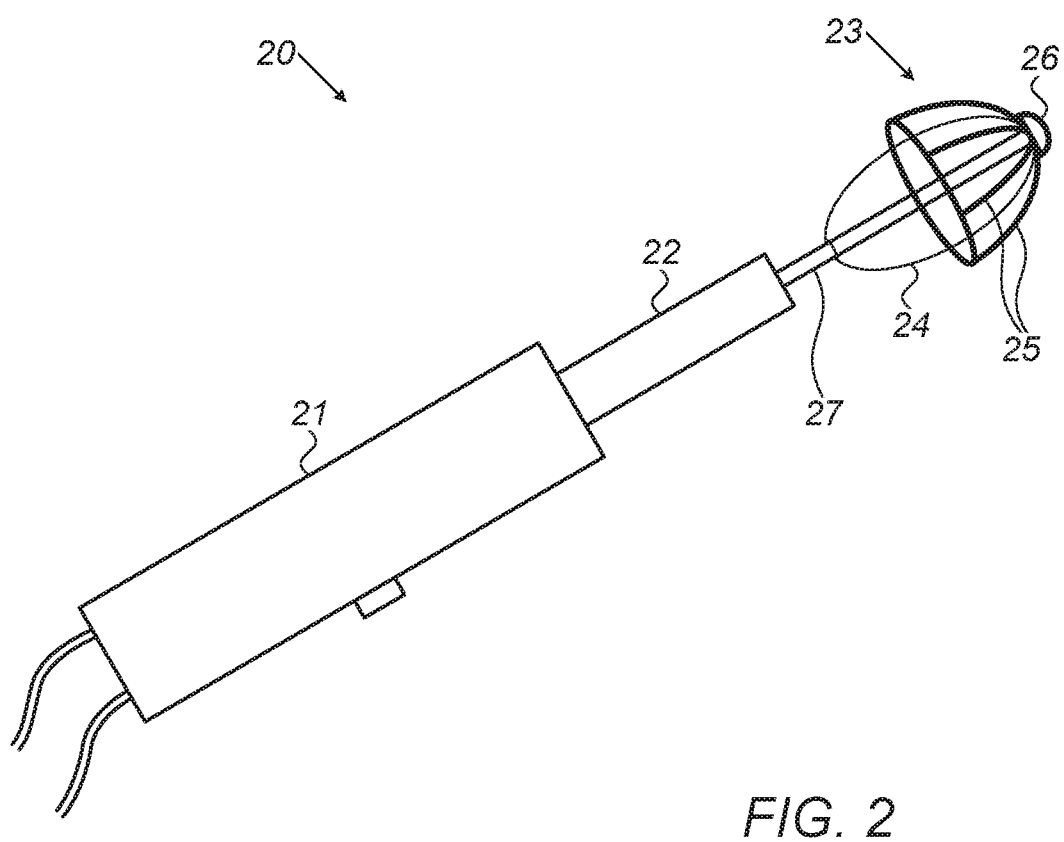
FIG. 2 is a simplified schematic side view of a TBP device in its deployed state, according to many embodiments.

FIG. 2 generally shows a device for producing pattern 18 in bladder 10, according to several embodiments.

More particularly, FIG. 2 is a simplified schematic side view of TBP device 20, comprising a handle 21, an external sheath 22, and a tool (or inner parts) 23, which may comprise at least an expandable element 24, an electrode structure 25, an atraumatic cap 26, and a shaft 27. Handle 21 may typically enable control over deployment of tool 23 out of sheath 22, and over expansion of expandable element 24 and thus over expansion of electrode structure 25. Device 20 is shown in FIG. 2 in its deployed state.

In use, device 20, in its crimped or un-deployed state, may typically be inserted into lumen 12 of a bladder 10 via urethra 15. It may then be deployed to achieve good apposition of electrode structure 15 with bladder wall 11, and energy, typically RF energy at approximately 500 Khz, may be transferred via the electrode structure to ablate tissue of bladder wall 11 thus creating ablation pattern 18. Retraction of tool 23 into external sheath 22 may then be done, and device 20 can be removed from the patient's body.

The prior applications incorporated herein, further describe other device embodiments for creating various embodiments of ablation pattern 18, as well as various improvements and modifications to them. Among other things, these improvements and modifications to the treatment devices include means for overcoming the great difference in diameter of urethra 15 versus bladder lumen 12, which may dictate a similar difference in the outer diameter of device 20 in its crimped state versus its deployed state. To the best of the knowledge of the inventors, such a difference in the outer diameter of an almost spherical device, in the magnitude of about ten-fold, is unparalleled by other medical devices.

An important feature of the treatment devices may include that ablation pattern 18 may comprise continuous elongate lines, and the devices 20 may comprise elongate conductors to produce said lines.

Another important feature of the treatment devices may include the creation of an ablation pattern 18 having at least one circumferential line C, and multiple longitudinal lines L.

Also described in these prior applications are devices which may be inserted at a very low profile, and may still create the desired ablation pattern.

The present disclosure describes additional methods and devices for improving upon the previously described methods and devices.

In many embodiments, a preliminary lavage step may be added to the treatment process. This preliminary lavage step may be used to remove the thin mucus layer present on the inner surface of urinary bladders. This thin mucus layer may be considered to act as a protective layer, actively secreted from the epithelial cells of the urinary bladder. Removing this layer may result with ablation lines that are thinner and more precise. When using RF ablation energy in the range of 500 Khz, the preliminary step of removing the mucus layer may improve the resulting ablation lines, resulting with less damage to the superficial cell layers, and an overall narrower lesion. When the mucus layer is not removed before the ablation is begun, occasional uneven warming of the surface may occur, and the resulting ablation lines may be less uniform and less predictable.

Figure 3A:
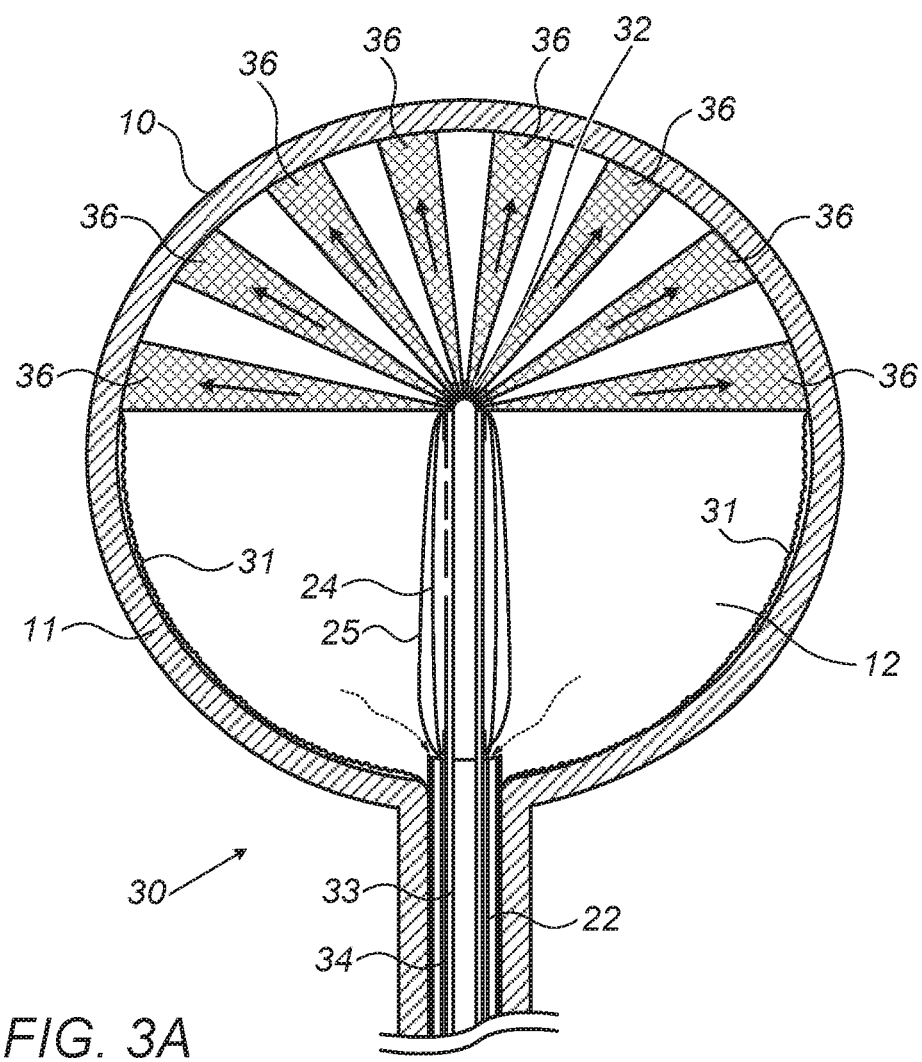
FIG. 3A is a simplified schematic longitudinal section of device for mucus removal from a bladder, according to many embodiments.
Figure 3B:
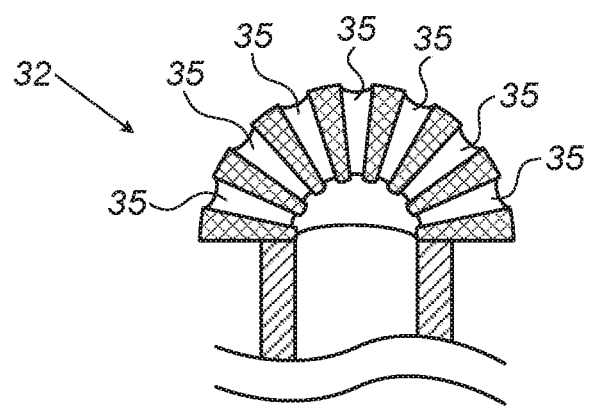
FIG. 3B is a simplified schematic longitudinal section a nozzle of a device for mucus removal from a bladder, according to many embodiments.

FIG. 3 depicts the mucus removal step using an embodiment of the TBP device.

More particularly, FIG. 3 is a simplified schematic longitudinal section of a urinary bladder 10, with a TBP-lavage device 30 inside it, which may be configured to remove mucus layer 31 from bladder wall 11.

TBP-lavage device 30 may be similar to device 20 with the difference that atraumatic tip 26 may be replaced with nozzle 32, which may be in fluid communication with central lumen 33 going through device 33. An outer lumen 34 may be in fluid communication with expandable element 24 which may be an inflatable balloon.

Nozzle 32 may comprise multiple openings 35. Pressurized fluid may flow through central lumen 33 and exit as a jet 36 through multiple openings 35. Jet 36 may be shaped as a narrow beam, a ring or a hemisphere. Alternatively, it may be shaped as a sheet or plain. A portion of jet 36, or all of it, may be directed distally, proximally, or in both directions.

Suction applied through the lumen of outer sheath 22 of device 30 may remove excess fluid introduced into bladder 10 by jet 36.

Although jet 36 was described as being produced by TBP device 30, it may be applied through a dedicated device, which may not be used for TBP.

The step of removing the mucus layer before applying treatment can be achieved in various ways. In some embodiments, the bladder may be initially inflated with air and subsequently, the urothelium may be sprayed with normal saline. Alternatively, the spraying of saline or other fluid may be performed without first filling the bladder with air, by use of a fluid jet strong enough to remove the mucus layer. Injection of jet 36 at one end of a catheter and aspiration at another end may create a flow within bladder lumen 12, which can aid in mucus layer removal. In some embodiments, the bladder may be filled with water containing a soap or solvent, and then drained (optionally washed again in saline or water). In some embodiments, a pharmacological agent such as n-acetyl cysteine may be infused into the bladder (diluted by water or saline). In some embodiments an acidic fluid (such as 0.1M HCL) may be first introduced into the bladder, which may cause denaturation of the mucus and easier removal. In some embodiments, the mucus may be mechanically removed, by swiping a cloth or cloth like or sponge like material over the inner bladder wall. In some embodiments, a protease enzyme may be used to remove the mucus. In some embodiments, hypertonic saline may be used. In some embodiments, a detergent may be used (for example 20% Triton X, or an equivalent). In some embodiments, a combination of the methods described above may be used. In some embodiments, an antiseptic solution, such as polidine or bethadine may be used. In some embodiments, alcohols and/or esters may be used. In some embodiments, pentachlorophenol, Medol, or an equivalent glycoprotein disruptive agent may be used.

An anesthetic agent may be added to the fluid to concomitantly induce local anesthesia. For example: ropivacaine can be added to a saline lavage, at a dosage that results in a concentration of 2 mg/mL ropivacaine in the lavage solution. In an additional example: 4% non-alkalinized (pH 6.0-7.0) lidocaine solution can be used for the lavage. In some embodiments, the local anesthetic may be instilled after the lavage, and kept in the bladder for 5 to 30 minutes before the deployed of the device. Alternatively, the local anesthetic agent may be delivered before the performed the lavage.

In some embodiments, precooling of the bladder may be achieved by instillation of cooled lavage fluids. Typically, this step may be performed following induction of local anesthesia to allow achieving temperatures as low as 4 degrees Celsius, well below the pain threshold (of approximately 20 degrees Celsius). The combination of lavage and cooling is intended to shorten the total procedure time. (Advantages of pre-cooling the bladder are detailed elsewhere in the current disclosure).

In some embodiments, the measured impedance may be used in order to guide the ablation process. When tissue is ablated, the impedance of the electrode/tissue circuit may rapidly rise signifying tissue charring. Other devices known in the art may use this phenomenon to guide ablation procedures, decreasing or stopping ablation when such a rise in impedance is measured. Another phenomenon is the gradual decrease in impedance that is seen during ablation, usually attributed to the heating of the tissue. The current disclosure describes ways to use the impedance measurement to guide ablation, specifically ablation of the urinary bladder. The inventors have found that when ablating within a porcine urinary bladder using a monopolar stainless steel wire electrode with a length of 25 mm, and a diameter of 0.2 mm, i.e. a contact surface area of 5 $mm^2$, the preliminary tissue impedance may usually be higher than 150 ohm, significantly higher than when ablating other tissue types. This is postulated to be due to the relatively impermeable intact urothelial layer, and an abrupt drop in impedance often observed is probably due to breaching of the urothelium. In other experimentation performed by the inventors (using a different electrode set, with a tissue contact area of roughly 5 $mm^2$), it was found that during a typical ablation the initial impedance measured is in the range of 120 ohms, and will drop by 25% (to 80 ohms) in the first second of ablation. The impedance will then continue to slowly decline reaching ~65 ohm in the next 5 seconds of ablation. The impedance will then essentially plateau at 60 ohms.

The present disclosure also describes a new method and device to create ablation in a urinary bladder, while monitoring the impedance. In some embodiments, the device may automatically reduce or cease ablation when the tissue impedance falls >40% of initial impedance value. Alternatively or in combination, the device may automatically abort ablation at a fixed time lag following the detection of such a decline. In some embodiments, the time lag may be 1 to 5 seconds, for example 2 seconds.

Alternatively or in combination, the ablation may be automatically stopped when the detected impedance plateaus, or at a fixed time lag following detection of such a plateau. A plateau may be defined as impedance decline at a rate that is below 5%/sec.

In some embodiments, an abrupt drop in impedance may be used to detect a breach of the epithelium. In some embodiments, high power may be applied until such a breach is detected, thereafter the ablation may be continued with standard energy settings, as known in the art. In some embodiments, an initial drop in impedance may be used to detect epithelium breach, and only after this drop is identified, a sudden rise may be used to detect tissue charring (and to guide the device and/or used to stop or reduce the ablation).

Figure 4:
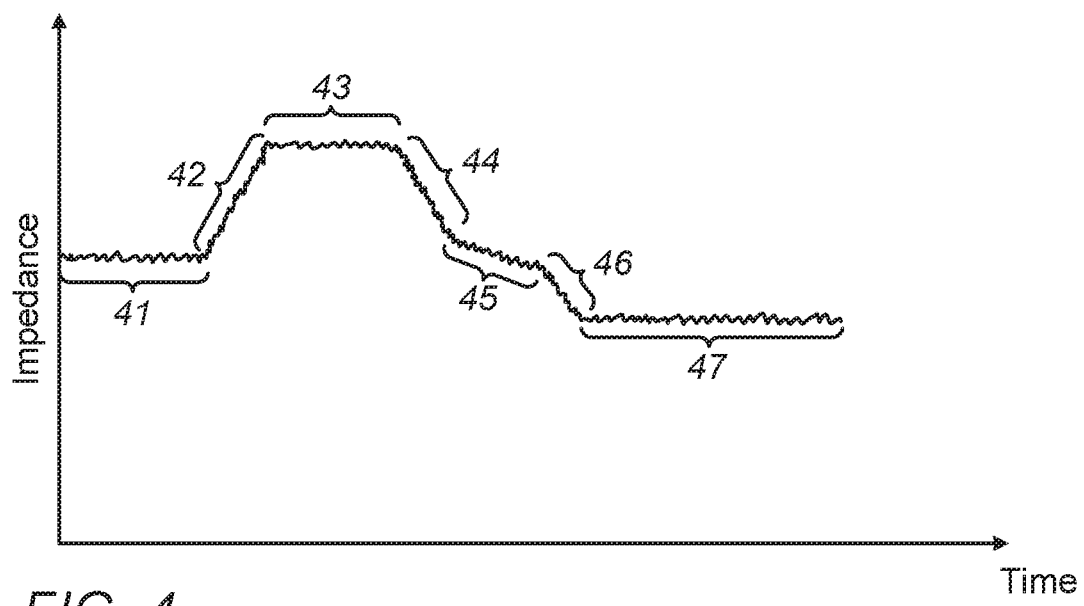
FIG. 4 is a schematic representation of theoretical changes in impedance during the TBP procedure, when a conductive bladder inflation fluid is used, according to many embodiments.
Figure 5:
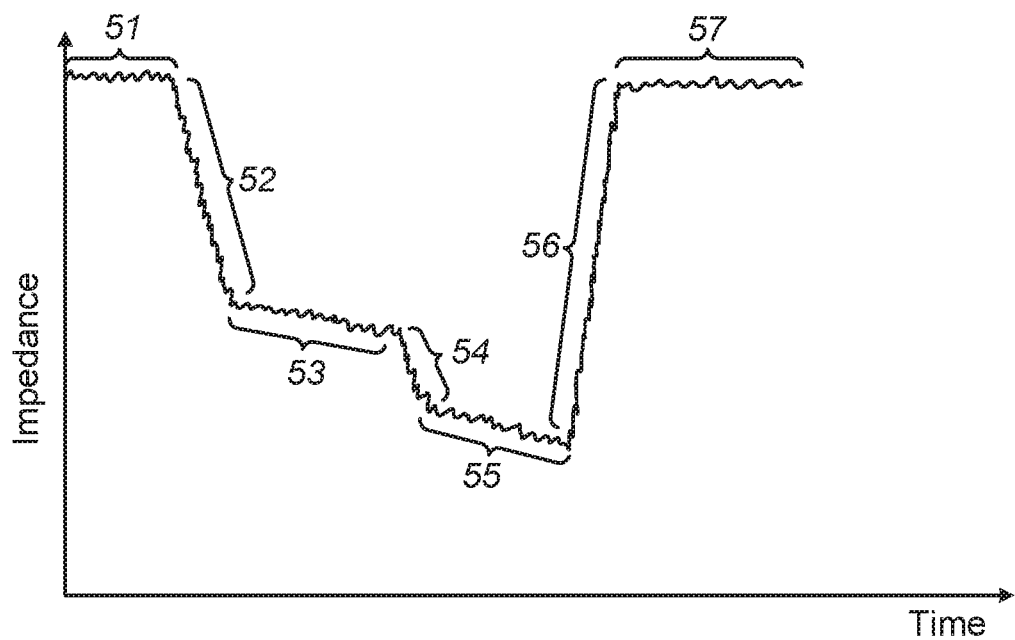
FIG. 5 is a schematic representation of theoretical changes in impedance during the TBP procedure, when a non-conductive bladder inflation fluid is used, according to many embodiments.

In some embodiments, impedance measurement may be used to assess electrode contact with the bladder wall during device deployment, and disconnection from it during retrieval. Among other factors, impedance changes may depend on the type of fluid used to inflate the bladder, as shown in FIGS. 4-5. In some embodiments, the impedance of the circuit may be assessed at different frequencies of alternating current.

The following is a description of embodiments in which a conductive fluid, such as saline or other crystalline solutions, may be used for inflation of the bladder.

FIG. 4 is a schematic representation of theoretical changes in impedance during the TBP procedure, when a conductive bladder inflation fluid is used.

More particularly, FIG. 4 is a theoretical, simplified graph, in which the horizontal axis represents time, and the vertical axis represents impedance, depicting theoretical impedance changes measured between electrodes of an embodiment of the invention, during a TBP procedure.

The impedances referred to in FIG. 4 may be measured between a treating electrode and a dispersive electrode of a device in the case of monopolar ablation, and between paired electrodes in the case of bipolar ablation.

The graph is not intended to represent actual impedance values, or ratios between them, only the trend of change between each stage and the one following it.

From left to right, the impedance graph in FIG. 4 shows the following general phases: baseline phase 41, contact phase 42, initial phase 43, urothelium breach phase 44, tissue warming phase 45, disconnection phase 46, and post procedure phase 47.

Baseline phase 41 represents the impedance which may be measured once the device is deployed in the bladder and before the electrodes contact the bladder wall. Since a conductive fluid is used, electrical current may flow from a treating electrode through the whole inner surface of the bladder to the dispersive electrode, in the case of monopolar ablation. In the case of bipolar ablation, electrical current may flow through the conductive fluid directly between the electrode poles. In both cases, impedance may be relatively low.

Contact phase 42 represents a rise in impedance which may be measured when the electrodes contact the bladder wall, thus decreasing the electrode surface area that is in contact with conductive fluid. In this situation, current between the electrodes must flow through the tissue covered by intact urothelium, and impedance may therefore increase relative to baseline phase 41, reaching a higher level of impedance represented by initial phase 43.

Urothelium breach phase 44 represents a possible drop in impedance which may be measured during ablation. Such a drop in impedance may occur due to a possible breach of the urothelium as a result of initiation of ablation. In this situation, current between the electrodes can flow through the tissue covered by breached urothelium, and impedance may therefore be lower than in initial phase 43.

Tissue warming phase 45 represents a possible further gradual decrease in impedance which may be measured during continued ablation. Such a gradual decrease in impedance may be caused as a result of increase in tissue conduction typically associated with tissue warming and/or modification.

Disconnection phase 46 represents a possible further drop in impedance which may be measured when the electrodes are disconnected from the bladder wall, thus increasing the electrode surface area that is in contact with conductive fluid. Since a conductive fluid is used, electrical current may flow from a treating electrode through the whole inner surface of the bladder to the dispersive electrode, in the case of monopolar ablation. In the case of bipolar ablation, electrical current may flow through the conductive fluid directly between the electrode poles. In both cases, impedance may be relatively low. In the case of monopolar ablation, impedance may be lower than it was initially in baseline phase 41, since the urothelium has been breached. The lowest level of impedance reached is represented by post procedure phase 47.

In some embodiments, an additional step of post ablation tissue cooling may be added. In these embodiments, the impedance during the cooling time may slowly rise. In some embodiments, the drop of impedance due to disengagement of the device from the bladder wall may be detected in comparison to the impedance measured following the tissue cooling phase.

In some embodiments, tissue contact may be deemed acceptable when impedance drops as the frequency rises. For example: a low current impedance test applied at 50 Hz, may be followed by a low current impedance test at 50 KHz. If the impedance in the latter is lower that the impedance of the former (by at least 10%), the tissue contact may be deemed acceptable.

In some embodiments, the ablation may not be initiated unless the impedance is high enough to signify acceptable contact with bladder tissue. For example: ablation may be withheld if the impedance measured is not at least 70% of the expected impedance.

In some embodiments, an "impedance reference" electrode may be used to guide the impedance derived decisions. In these cases, the reference electrodes may be chosen to be electrodes that are positioned at the distal end of the probe, so that good tissue contact can be ensured by applying axial force on the probe against the bladder wall. Once such a reference value is obtained, the impedance of other electrodes may be compared to the reference electrode, to ensure good contact.

In some embodiments, the disconnection of the electrode from the tissue may be assessed before retrieving the device from within the urinary bladder. In some embodiments, this retrieval may be performed following the ablation, after the tissue may have been modified. Thus, in some embodiments, the impedance measurement used to assess the tissue contact may compare a current reading to the previous reading before the ablation was performed. In some embodiments, the disconnection of the electrode from the tissue may be assessed by comparing a previous reading taken before the ablation was applied, to the current reading. In some embodiments, more than 5 seconds may be allowed to elapse from the end of ablation to the next reading of impedance, to allow the bladder and electrodes to cool before the impedance measurement.

For example, after ablation has been performed and the electrodes were supposed to be disconnected from the bladder wall, the device may measure an impedance of 85 ohm per 10 $mm^2$ electrode contact area. The device may then compare this value to an impedance value measured at the same location, before the ablation was applied (but after contact between the device and the bladder is established), for example 100 ohm per the same electrode contact area. In this case, although a drop in impedance was detected, it is well within the expected range of impedance drop that may occur without the electrode disconnecting from the tissue, thus the device may alert that the disconnection from the tissue is incomplete.

In some embodiments, the desired sequence of impedance measurements may include an initial rise in impedance as the tissue contact is established, a drop when the epithelium is breached, a further reduction when the tissue is modified, a rise in impedance during tissue and electrodes cooling, and a last drop in impedance when the electrode is successfully detached from the tissue.

The following is a description of embodiments in which a non-conductive fluid (NCF), such as distilled water, glycine or sorbitol, may be used for inflation of the bladder, as commonly done in urological electro-cautery procedures.

FIG. 5 is a schematic representation of theoretical changes in impedance during the TBP procedure, when a non-conductive bladder inflation fluid is used. The graph in FIG. 5 is similar to that in FIG. 4, with the difference that a non-conductive fluid is used; therefore the phases are named with the same titles as in FIG. 4, with the addition of "NCF".

More particularly, FIG. 5 is a theoretical, simplified graph, in which the horizontal axis represents time, and the vertical axis represents impedance, depicting theoretical impedance changes measured between electrodes of an embodiment of the invention, during a TBP procedure.

The impedances referred to in FIG. 5 may be measured between a treating electrode and a dispersive electrode of a device in the case of monopolar ablation, and between paired electrodes in the case of bipolar ablation.

The graph is not intended to represent actual impedance values, or ratios between them, only the trend of change between each stage and the one following it.

From left to right, the impedance graph in FIG. 5 shows the following general phases: NCF baseline phase 51, NCF contact phase 52, NCF initial phase 53, NCF urothelium breach phase 54, NCF tissue warming phase 55, NCF disconnection phase 56, NCF post procedure phase 57.

NCF baseline phase 51 represents the impedance which may be measured once the device is deployed in the bladder and before the electrodes contact the bladder wall. Since non-conductive fluid is used, electrical current may not flow between the electrodes. Impedance may therefore be relatively very high in either monopolar, or bipolar modes.

NCF contact phase 52 represents a decrease in impedance which may be measured when the electrodes contact the bladder wall. In this situation, current between the electrodes may flow through the tissue covered by intact urothelium, and impedance may therefore decrease relative to NCF baseline phase 51, reaching a lower level of impedance represented by NCF initial phase 53, although impedance may still remain relatively high;

NCF urothelium breach phase 54 represents a possible drop in impedance which may be measured during ablation. Such a drop in impedance may occur due to a possible breach of the urothelium as a result of initiation of ablation. In this situation, current between the electrodes can flow through the tissue covered by breached urothelium, and impedance may therefore be lower than in NCF initial phase 53.

NCF tissue warming phase 55 represents a possible further gradual decrease in impedance which may be measured during continued ablation. Such a gradual decrease in impedance may be caused as a result of increase in tissue conduction typically associated with tissue warming and/or modification.

NCF disconnection phase 56 represents a possible increase in impedance which may be measured when the electrodes are disconnected from the bladder wall. Since non-conductive fluid is used, electrical current may not flow between the electrodes. Impedance may therefore be relatively very high in either monopolar, or bipolar modes. The maximal level of impedance reached is represented by NCF post procedure phase 57.

In some embodiments, an additional step of post ablation tissue cooling may be added. In these embodiments, the impedance during the cooling time may slowly rise. In some embodiments, the rise of impedance due to disengagement of the device from the bladder wall may be detected in comparison to the impedance measured following the tissue cooling phase.

In some embodiments, tissue contact may be deemed acceptable when impedance drops as the frequency rises.

In some embodiments, the ablation may not be initiated unless the impedance is low enough to signify acceptable contact with bladder tissue.

In some embodiments, the disconnection of the electrode from the tissue may be assessed before retrieving the device from within the urinary bladder. In some embodiments, this retrieval may be performed following the ablation, after the tissue may have been modified. Thus, in some embodiments, the impedance measurement used to assess the tissue contact may compare a current reading to the previous reading before the ablation was performed. In some embodiments, the disconnection of the electrode from the tissue may be assessed by comparing a previous reading taken before the ablation was applied, to the current reading.

For example, after ablation has been performed and the electrodes were supposed to be disconnected from the bladder wall, the device may measure an impedance of 80 ohm per 10 mm$^2$ electrode contact area. The device may then compare this value to an impedance value measured at the same location, before the contact was established, for example >300 ohm per the same electrode contact area, before the ablation was applied, for example 100 ohm per the same electrode contact area, and after ablation was applied, for example 70 ohm per the same electrode contact area. In this case, although an increase in impedance may be detected compared to the post ablation measurement, it may be insufficient compared to what is expected after disconnection, thus the device may alert that the disconnection from the tissue is incomplete.

In some embodiments, the desired sequence of impedance measurements may include an initial drop in impedance as the tissue contact is established, a second drop when the epithelium is breached, a further reduction when the tissue is modified, and an increase in impedance when the electrode is successfully detached from the tissue.

In some embodiments, prior to ablation, the bladder may be filled with a conductive fluid (such as saline, etc.), but after ablation was applied, for the detachment stage, the bladder may be filled with non-conductive material (such as air or glycine).

In some embodiments, once the second (non-conductive) agent may be instilled in the bladder, the impedance may be expected to significantly rise, signifying detachment of the electrodes.

In some embodiments, the device may comprise four or more electrodes. In some embodiments, the impedance of one electrode may be compared to the impedance of another electrode (or the impedance of a first electrode pair may be compared to the impedance of a second electrodes pair). Thus, when using a conductive fluid, if a significantly higher impedance is measured for one electrode pair compared to other electrode pairs, this may signify that the first pair has not disconnected from the bladder tissue. Conversely, when using a non-conductive fluid, measurement of a significantly lower impedance for one electrode pair compared to other electrode pairs, may signify that the first pair has not disconnected from the bladder tissue.

In some embodiments, while electrodes may still be in contact with the bladder wall after ablation, this contact may be "light" and may not cause any interference with retrieving the device.

In some embodiments, to differentiate "light", inconsequent contact, from "tight" contact (i.e. contact that is caused by adherence of electrodes to tissue) that might interfere with retrieval—the device may be slightly retracted and/or moved (i.e., tilted up or down, slightly turned, etc.), while the impedance may be continuously monitored. If the manipulations above result in impedance changes that are more than 10% of the measured impedance, the contact may be deemed "light" and retraction can be undertaken safely.

Figure 6:
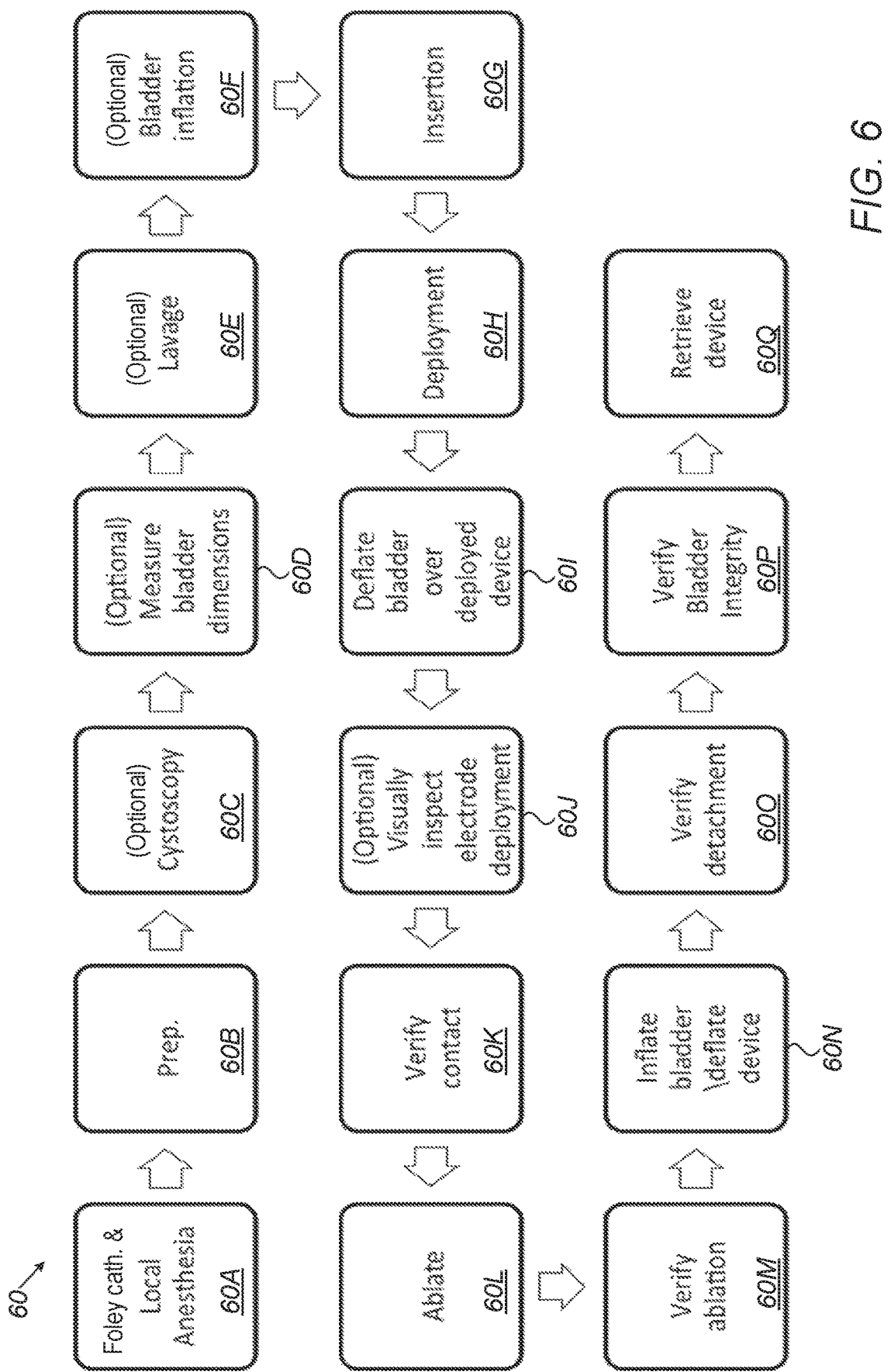
FIG. 6 is a flow chart depicting the stages of a TBP procedure, according to many embodiments.

The TBP procedure stages are described in the flow chart shown in FIG. 6.

More particularly, FIG. 6 is a flow chart with multiple steps that may be included in a TBP procedure 60.

Step 60A may comprise insertion of a Foley catheter into the patient's bladder. Typically, prior to bladder catheterization, the patient's external urethral meatus may be cleansed and draped. The bladder may be drained, and a local anesthetic solution such as 50 cc of lidocaine with 10 cc of bicarbonate may be instilled through the catheter. Measurement of the urethral length may be performed using the Foley catheter, by inflating its balloon, and lightly pulling on the catheter to ensure the balloon is seated at the bladder neck. Location of the external urethral meatus may be marked on the catheter, and the distance from the balloon to the marking may be measured following catheter removal. The patient may then typically be allowed to wait for 20-30 minutes to allow for induction of anesthesia.

Step 60B may comprise preparation of the patient for cystoscopy and/or the procedure. This may include positioning of the patient in a relaxed lithotomy position, with back supine on table and thighs lifted at 60 degrees from horizontal, and cleansing and sterile draping as customary.

The TBP device may typically be prepared at this stage. Such preparation may include inspection of the device, and marking of the previously measured urethral length on the external sheath of the device, using a sterile marker, or by locking a slideable element to said external sheath.

Step 60C may optionally comprise performing a cystoscopy. This step may optionally be performed at a prior physician visit, or may alternatively be omitted. Cystoscopy may enable ruling out anatomical abnormalities of the lower urinary tract such as diverticula, presence of tumors, or presence of calculi. Optional steps 60D and 60E may be performed as part of step 60C.

Step 60CD may optionally comprise performing a measurement of internal bladder dimensions as will be further described below. Decisions regarding the procedure, such as whether the patient is appropriate to undergo the procedure, or whether a specific size of device may be used, may be taken based on such measurements.

Step 60E may optionally comprise performing lavage of the inner surface of the bladder fur removal of a mucus layer, as was described above.

Step 60F may optionally comprise inflating the bladder with a conductive or non-conductive fluid. Such inflation of the bladder may make deployment of the device within the bladder easier and safer, however the procedure may also be performed without this step. Alternatively and optionally, this step may be performed via the external sheath of the device, after step 60G (i.e. after insertion).

Step 60G may comprise insertion of the device through the urethra into the bladder. Typically to facilitate passage through the urethra, a lubricant gel may be applied to the outer surface of the device shaft. Such gel may preferably be water based in order to avoid interfering with electrical conduction in case some of this gel enters the bladder itself or reaches the device electrodes.

Step 60H may comprise deployment of the device within the bladder. Typically this may include passing the expandable element of the device with the electrodes, out of the external sheath, and expansion of the expandable element. Optionally, if the expandable element comprises a balloon, its expansion may be performed by transfer of fluid from the bladder into the balloon.

Step 60I may comprise deflation of the bladder over the deployed inflated device. Typically this may be done by draining the bladder around the device through a port opening into the external sheath. If the bladder was inflated prior to device insertion, there may be a large volume of fluid that may need to be removed. If the bladder was empty prior to device insertion, the volume of fluid may be small; however, this step may be important in order to ensure optimal contact between the electrodes and bladder wall.

Step 60J may optionally comprise visual inspection of satisfactory deployment of the electrodes. This may be performed optically via the device itself in some embodiments, or using external imaging such as ultrasound or fluoroscopy, in other embodiments.

Step 60K may comprise verification of electrode contact with the bladder wall. This may be performed by measurement of impedance as described above, by measurement of contact force, or other methods as known in the art.

Step 60L may comprise ablation of the required lesion pattern. Typically this step may be initiated by the user, by activation of a footswitch, a button on the device itself, a graphical user interface on a screen, or other method as known in the art.

Step 60M may optionally comprise verification of adequacy of the ablation. Typically this step may be performed by measuring impedances across ablation lines, by measuring response to stimulation at various location on the bladder, or other methods.

Step 60N may comprise inflation of the bladder around the device, optionally concomitantly with deflation or contraction of the expandable element. If the expandable element is a balloon, this step may be performed for example by transfer of fluid drained from the balloon into the bladder via the external sheath port, or by inflation of fluid into the bladder in a volume similar to that removed from the device. This step may ensure that the bladder wall has detached from the electrodes prior to retraction of the device.

Step 60O may comprise verification of electrode detachment from the bladder wall. Similar to step 30, this may be performed by measurement of impedance as described above, by measurement of contact force, or other methods as known in the art.

Step 60P may comprise verification of bladder integrity. This may be performed for example by inflation of the bladder with concomitant measurement of inflated volume and pressure, which may be done via the external sheath port. This may enable calculation of bladder compliance and maximal capacity, both of which typically are not expected to increase following the procedure. Significantly increased compliance or bladder capacity may indicate a perforation of the bladder. The bladder may subsequently be drained, and the removed volume compared to the inflated volume. A significant decrease in the volume removed compared to that inflated, may also indicate bladder perforation. Step 60P may be performed before or after step 60Q—device retrieval. In case it is performed after step 60Q, inflation may be done via a Foley catheter or a cystoscope.

Step 60Q may comprise retrieval of the device. Typically this may include retraction of the balloon with electrodes into the external sheath, and subsequent removal of the sheath from the urethra. Following retrieval, the device may typically be examined for integrity.

Another aspect of the present disclosure relates to avoidance of ablation at certain areas of the bladder. In particular, it may be important to avoid ablating the ureters, to prevent inadvertent changes that might induce urine reflux and/or increased resistance to the flow of urine from the kidneys. Areas of the ureters that may be avoided of ablation include the ureteral orifices, as well as the part of the ureters that travels within the bladder wall.

Prior to ending at the ureteral orifice, the ureters travel through the bladder wall, coursing through the muscle and having a segment that tunnels beneath the mucosa. This anatomical arrangement is considered to be functionally important in preventing reflux of urine from the bladder back into the ureters (and kidneys). When the bladder fills, the increased bladder pressure compresses the ureteral tunnels that lie immediately beneath the mucosa and effectively act as a valve, blocking backflow.

The section of the ureter that travels within the bladder wall is described as "oblique" and its length increases with age. Much anatomic variation exists, and the exact length of this segment in adults is not well studied.

The present disclosure further describes methods and devices intended to perform transurethral bladder partitioning, while avoiding ablation of the ureters, including their intramural parts.

In designing the device, schematic spherical model of the bladder and trigone was used to represent the three dimensional relationships between the ureteral orifices and the bladder neck, to accommodate variations in bladder anatomy and volume. Calculations were performed with different bladder volumes (in the range of 150 cc to 250 cc), and different bladder neck to ureteral orifice distances (30 mm to 50 mm).

When considering the "worst case scenario", where the ureteral orifices are distant from the bladder neck, and the intramural part of the ureter is exceptionally long—it was found that ablation along the equator of the bladder might be close to the ureters.

The present disclosure further describes methods and devices intended to avoid the risk of ureteral injury. Principally, two different approaches are described. The first approach relies on pre-measuring of the anatomy (to choose the right device and/or to abort the procedure if risk to the ureters is detected). The second approach may include avoiding ablation along the equator, by tilting of the equatorial line to be closer to the bladder neck anteriorly and further up the bladder at the posterior aspect (where the ureters are located).

In some embodiments, step 60D of performing the cystoscopy may further comprise filling the bladder to a volume of 150 cc-250 cc and examining the position of the ureteral orifices at this volume.

In some embodiments, described in FIG. 3, the distance from the bladder neck to the ureteral orifice may be measured by a marked catheter (resembling a ruler) which may be advanced through the working channel of the cystoscope.

Figure 7:
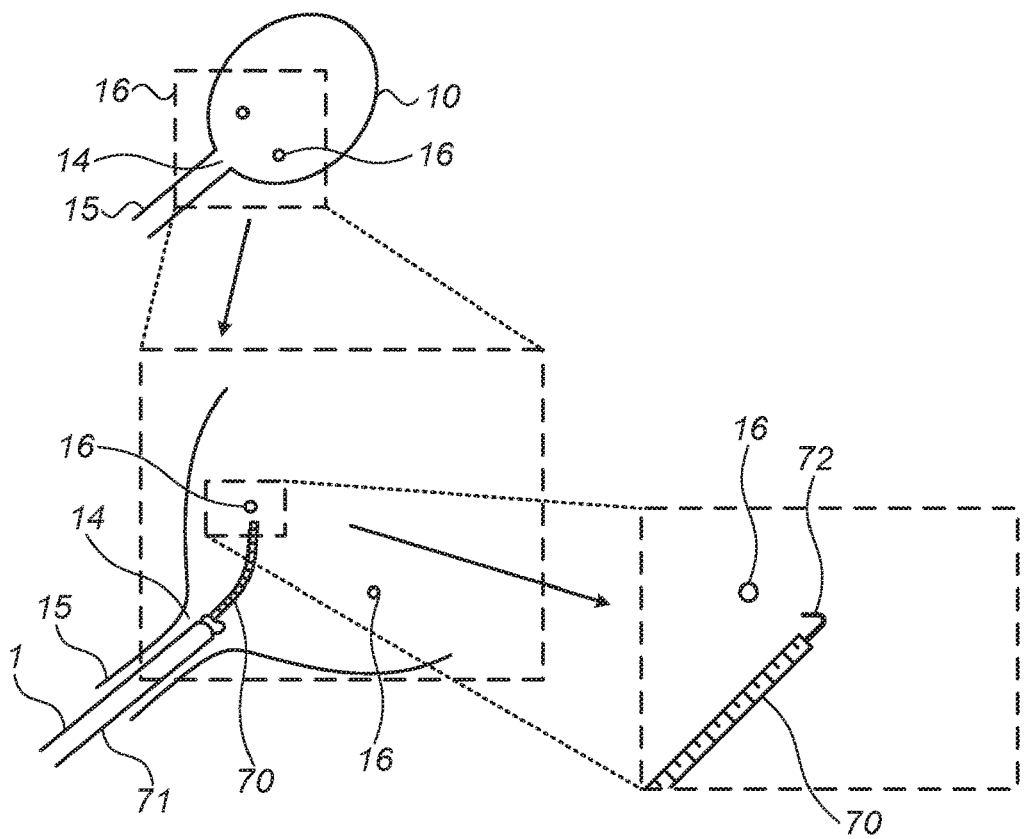
FIG. 7 is a simplified schematic drawing of a ruler measurement tool, according to many embodiments.

More particularly, FIG. 7 is a schematic simplified section of a bladder 10 in the coronal plain with two levels of zoom-in windows. Bladder 10 is seen with two ureteral orifices 16, bladder outlet 15, and urethra 15.

Ruler 70 is seen introduced via a cystoscope 72 into the bladder lumen.

Ruler 70 may comprise a dedicated disposable catheter that may include distance markings and optionally a gentle hook 72 that may allow the operator to anchor ruler 70 at the height of ureteral orifice 16. Ruler 70 may be hooked to the tissue of bladder wall 11 at the place chosen by the operator and cystoscope 71 may subsequently be pulled back to bladder outlet 14 (while ruler 70 is still hooked at ureteral orifice 16), thus easily visualizing the distance markings of ruler 70, at the bladder neck, or at the proximal opening of the working channel of cystoscope 71. Ruler 70 may then be un-hooked by pushing it slightly forward and subsequently gently retrieving it back into cystoscope 71. In some embodiments, hook 72 may be flexible enough to be aligned with the shaft of Ruler 70 during passage through cystoscope 71 (pressed within the shaft). In some embodiments, hook 72 may be soft enough to re-align with ruler 70 when pulled proximally into ruler 70, effectively protruding beyond the tip of ruler 70, thus releasing the hook from the tissue without need for any special manipulation. In some embodiments, anchoring to the bladder wall may be achieved by gentle suction. In some embodiments, disconnection of ruler 70 from bladder wall 11 may be achieved by applying positive pressure.

In other embodiments, a measuring tool may comprise a marked catheter inserted into the ureter 17 to a specific distance. Optionally, this catheter may include a radially protruding element such as a small balloon, which may be inflated before insertion into the ureter, and may serve both to prevent insertion of the catheter into the ureter deeper than intended, and as a reference point for measurement, if fluoroscopy is used. By pushing this catheter distally while moving proximally with the cystoscope, the physician can make sure that the catheter stays in place relative to the ureteral orifice, and the distance between the ureteral orifice and bladder outlet can be directly measured by counting the markings on the catheter, or inferred from the markings on the part of the catheter exiting the proximal opening of the working channel of the cystoscope. In some embodiments, the bladder neck to ureteral orifice distance is not measured, only verified to be less than a predetermined value, such as 3 cm. In these embodiments, a sizing catheter is introduced through a cystoscope and set to protrude to a fixed distance, such as 3 cm. The operator places the tip of the scope at the bladder neck, and can then readily see if the distance from the bladder neck to the ureteral orifice is indeed below this preset value, by seeing the sizing catheter extending beyond the ureteral orifice. In some embodiments, standard ureteral catheters can be used for sizing the bladder neck to ureteral orifice distance.

Figure 8A:
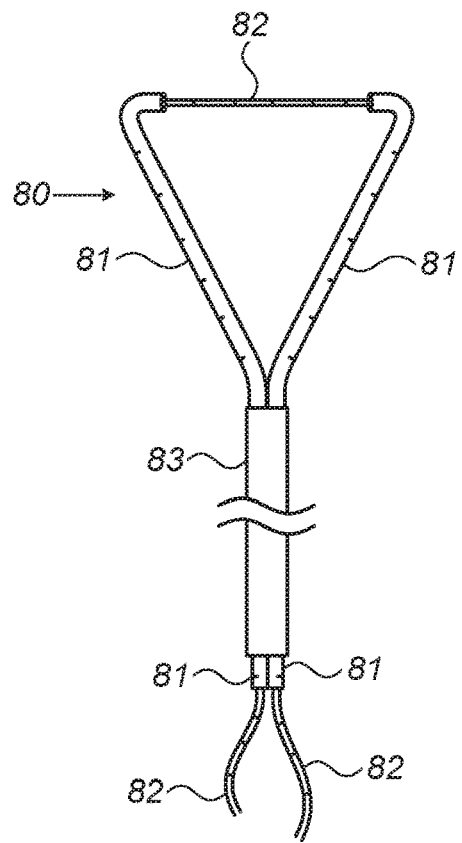
FIG. 8A is a simplified schematic front view of a Triangular Measurement Tool (TMT), according to many embodiments.
Figure 8B:
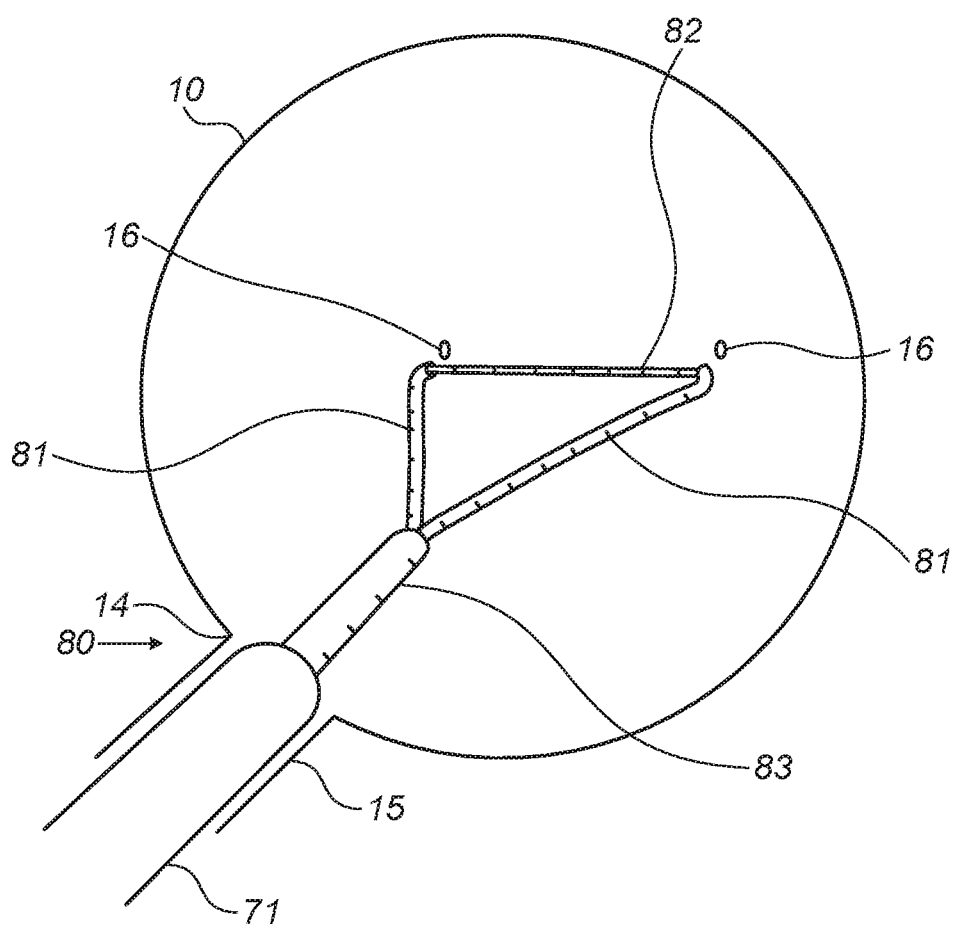
FIG. 8B is a simplified schematic front three dimensional view of Triangular Measurement Tool (TMT) in use, according to many embodiments.

In an embodiment of a measuring tool shown in FIGS. 8A-8B, a Triangular Measurement Tool (TMT) is used.

More particularly, FIG. 8A is a front view of TMT 80 comprising at least two semi rigid hollow tubes 81, a wire 82, and s sheath 83. Hollow tubes 81 may be connected to each other along at least a part of their length and slideably positioned inside sheath 83. The distal segment of hollow tubes 81 may have an outward bend so that tubes 81 tend to move away from each other when pushed out of sheath 83, and move towards each other when pulled into sheath 83. Tubes 81 may be manufactured from nitinol or other shape memory alloy, and heat treated to attain the desired outward tendency. Alternatively or in combination, tubes 81 may be made of any biocompatible polymer with the appropriate mechanical properties such as PEEK, PEBAX etc. Sheath 83 may be made of the same polymers as well, and may typically have an outer diameter compatible with a working channel of a cystoscope, e.g. 4-6 French.

Wire 82 (typically made of nitinol, stainless steel, or other metal or polymer wire) may be threaded through tubes 81 and may extend through their distal openings and connect them, such that when the device is deployed, i.e. when tubes 81 are pushed distally out of sheath 83, tubes 81 and wire 82 may form a triangle. Wire 82, tubes 81, and sheath 83 may be marked at known intervals.

Limiting the sliding of wire 82 into the tubes from the proximal side, may limit expansion of the triangle base (the wire part). This may be done manually or using a button that may release the wire, or by other wire control mechanisms as known in the art.

FIG. 8B depicts use of TMT 80. More particularly, FIG. 8B is a simplified schematic 3D depiction of TMT 80, showing the outline of bladder 10 having urethra 15 through which a cystoscope 71 may be inserted.

In use, TMT 80 may be inserted through the working channel of cystoscope 71. Tubes 81 may be pushed distally and wire 82 may be released to allow spreading of tubes 81 laterally, until tube 81 distal ends may be adjacent to ureteral orifices 16. Wire 82 may be clamped so the triangle base stays at a constant length. As described with the previous embodiment, cystoscope 71 may be moved back to bladder outlet 14 while TNT 80 is kept pushed against the posterior bladder wall, so that the triangle base stays between ureteral orifices 16.

Both the distance between ureteral orifices 16 and the distance between bladder outlet 14 and ureteral orifices 16 can be measured in this way by counting the markings on wire 82, tubes 82, and sheath 83 inside the bladder, or by noting the change in their position at the back end of the cystoscope.

Yet another embodiment of a measurement tool for measuring bladder dimensions is depicted in FIG. 9011, in which the measurement tool may comprise a balloon mounted on a shaft.

Figure 9:
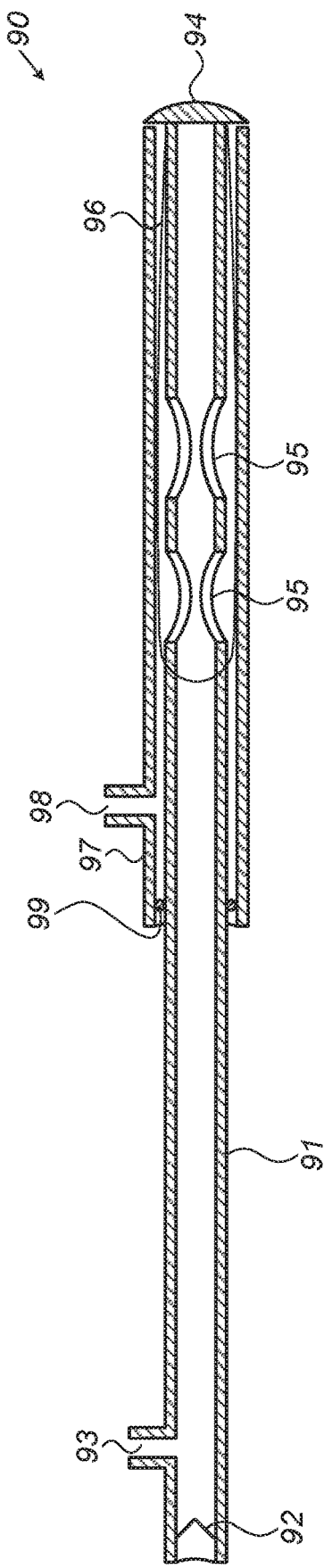
FIG. 9 is a simplified schematic longitudinal section of an Inflatable Measurement Tool (IMT) in its deflated state, according to many embodiments.

More particularly, FIG. 9 is a longitudinal section of Inflatable Measurement Tool (IMT) 90, comprising shaft 91 having valve 92 and port 93 at its proximal end, and cap 94 at its distal end. Proximal to its distal end, apertures 95 may maintain fluid communication between the lumen of shaft 91 and a measurement balloon 96 mounted on shaft 91. Balloon 96 with shaft 91 may be slideably disposed within sheath 97 having port 98 adjacent its proximal end, and gasket 99 proximal to port 98, such that a fluid seal may be maintained between shaft 91 and sheath 97.

The inner diameter of shaft 91 may be large enough for insertion of a standard cystoscope optical tool, i.e. preferably approximately 4 mm internal diameter. The length of shaft 91 may be compatible with a standard cystoscope, i.e. approximately 30 cm. Valve 92 may be a one way valve allowing introduction of a cystoscope while preventing leakage of fluid.

Figure 10:
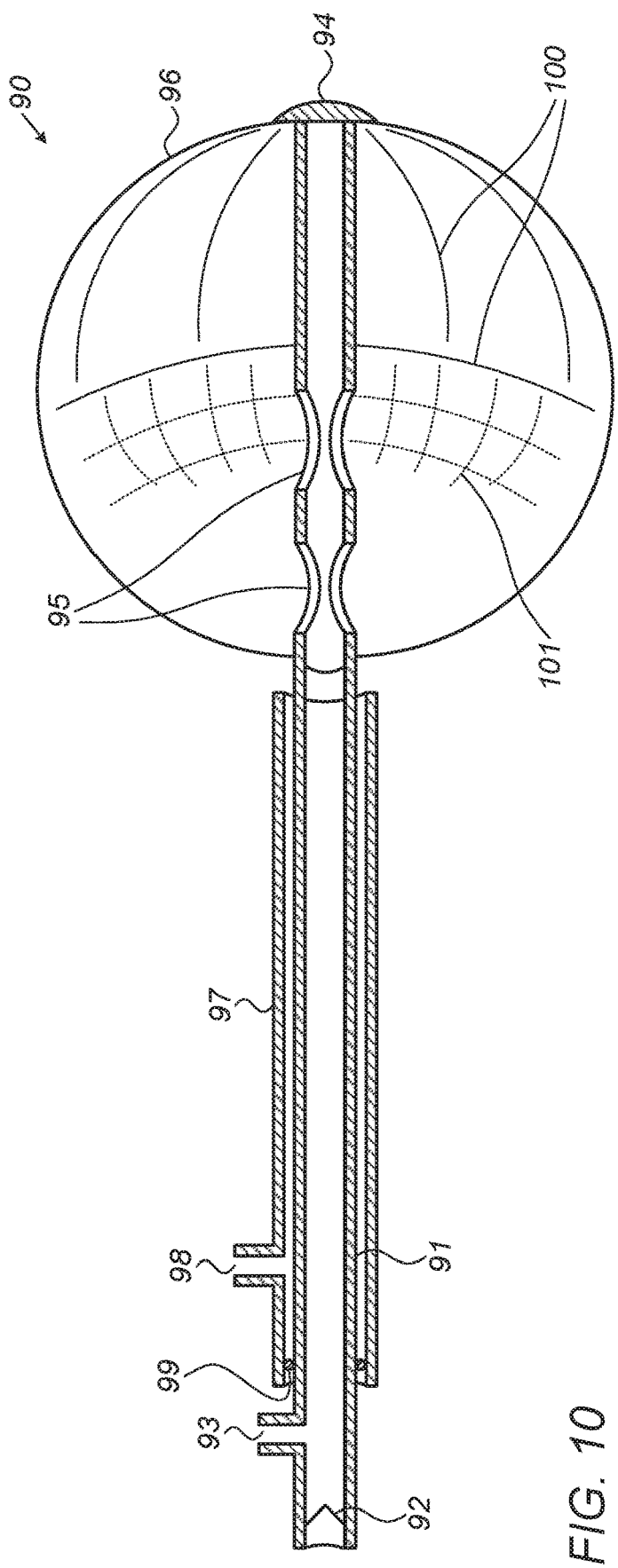
FIG. 10 is a simplified schematic longitudinal section of an Inflatable Measurement Tool (IMT) in its inflated state, according to many embodiments.

FIG. 10 shows a device with the same elements as that of FIG. 9, except that balloon 96 is inflated. Balloon 96 may be transparent, may have the same dimensions as balloon 24 of TBP device 20, and may have markings 100 delineating the location of the electrode structure 25 on at least part of its surface, preferably the posterior part, and optionally additional markings or even a grid 101 at known distances from the electrodes. A number or sign identifying each electrode may further be added, to enable identification of the specific electrodes that will be placed at specific locations, allowing inactivation of individual electrodes that are at an undesirable location.

Figure 11:
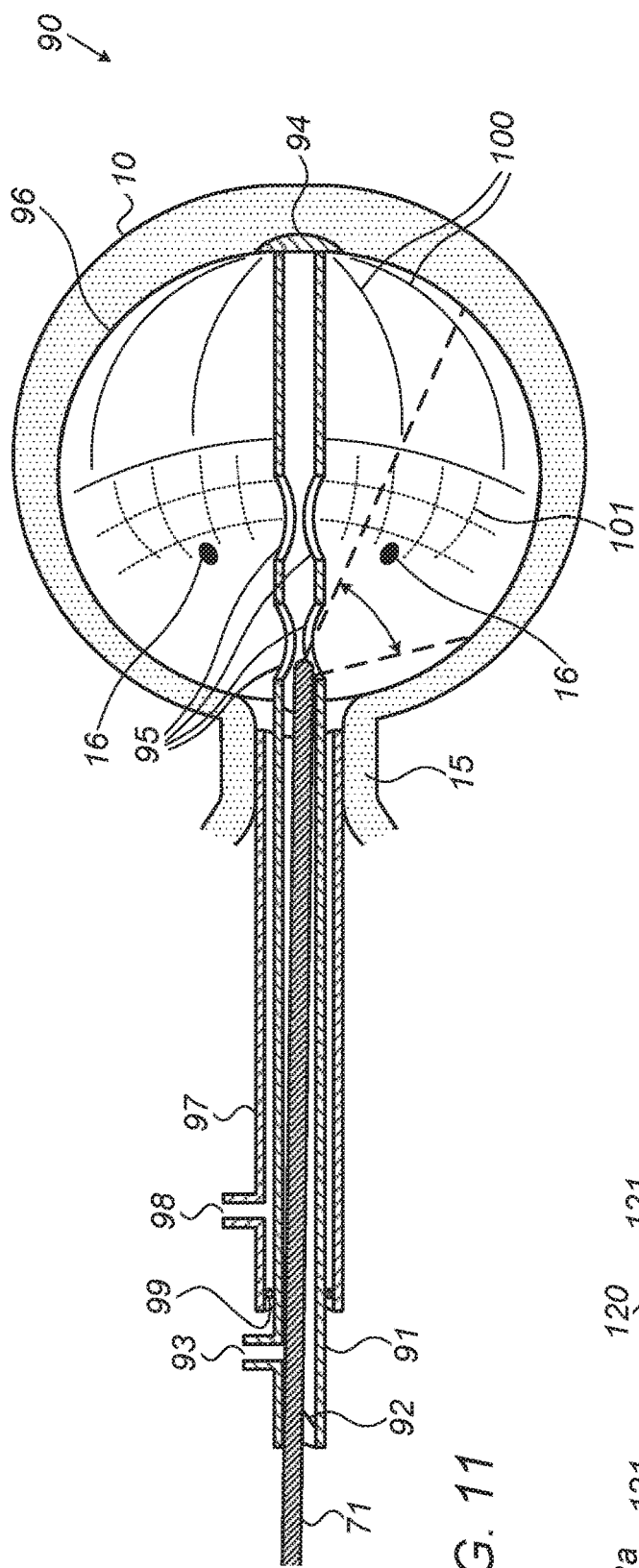
FIG. 11 is a simplified schematic longitudinal section of an Inflatable Measurement Tool (IMT) in its inflated state in use inside a bladder, according to many embodiments.

FIG. 11 depicts use of IMT 90 in a bladder.

More particularly FIG. 11 is a longitudinal cross section of IMT 90 and bladder 10 in the coronal plain, showing IMT 90 in its inflated state, and with cystoscope 71 passed through shaft 91 until its distal end is adjacent aperture 95.

In use, following initial standard cystoscopy, IMT 90 may be inserted into the bladder and inflated to the target volume in the same manner as may be done with the treatment device (the bladder may be drained, inflated to a known volume, balloon 96 may be inflated while the bladder may be drained until it rests on balloon 96). Once inflated, a cystoscope may be inserted through shaft 91 into the balloon until the inside of the bladder can be viewed through any of apertures 95. When lens of cystoscope 71 is brought to the level of an aperture 95, markings 100 of the anticipated electrode locations, grid 101, and ureteral orifices 16 may be observed via transparent balloon 96, such that the user may make sure the distance between markings 100 and ureteral orifices 16 is sufficient.

In some embodiments, the apertures at the distal end of the shaft 91 are large enough as to allow substantially undisturbed view through the tube. In some embodiments, a reflective coating is added on the inner surface of the upper pole of balloon 96. Thus, a cystoscope placed within the tube and directed at the upper pole of the balloon can easily visualize the reflection of the lower part of the bladder, the balloon and electrode markings.

If the electrode markings are found to be too close to the ureteral orifices, the procedure may be aborted, or a different device with more appropriate dimensions or electrode configuration may be used.

Alternatively, a decision can be made such as to inactivate specific electrodes that may be expected to be excessively close to ureteral orifices 16.

Alternatively, a decision can be made such as to place a protection element/shield over the ureters as will be described below, or any other measure to protect the ureters.

In some embodiments, the TBP device may further include means for insertion of a scope into balloon or expandable element 24 of the TBP device 20 or 30. This may enable viewing bladder wall 11 through balloon or expandable element 24 during or following deployment, making sure the electrodes were actually deployed properly and are situated correctly in relation to the specific patient's anatomy. Such means may include a unidirectional valve at the proximal end of the balloon inflation tube, a transparent balloon inflation tube, and or apertures in the balloon inflation tube, similar to those described for IMT 90 above.

The disclosure further describes protection elements, which may be used to prevent unintentional ablation of areas such as the ureteral orifices. As shown in FIGS. 12A-12D, the protection elements, or shields, may comprise a thin layer of insulating material such as nylon, and may be attached to a flexible frame, which may be made of nitinol, plastic, or other appropriately flexible material.

Figure 12B:
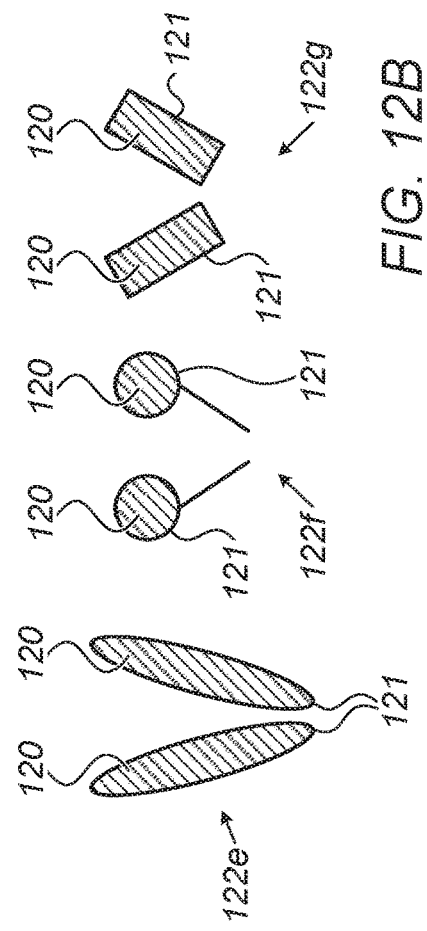
FIG. 12B is a schematic simplified front view of protection elements, according to many embodiments.
Figure 12A:
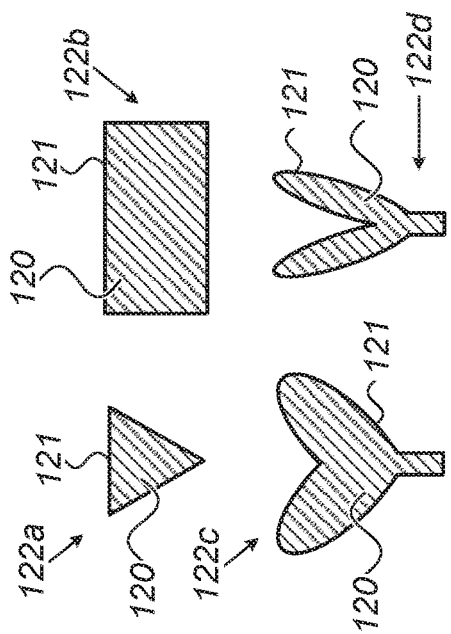
FIG. 12A is a schematic simplified front view of protection elements, according to many embodiments.

More particularly, FIG. 12A is a schematic simplified front view of protection elements 122a-g, each comprising insulating material 120 and flexible frame 121.

The shape of protection elements 122a, 122b, 122c, 122d, 122e, 122f, 122g may be mostly determined by flexible frame 121, and may take various forms, for example a triangle 122a, oblong 122b, "heart" shape 122c, or "V" 122d, each such single protection element having dimensions sufficient to cover both ureteral orifices 16.

FIG. 12B is a schematic simplified front view of protection elements 122e, 122f, 122g, each comprising insulating material 120 and flexible frame 121.

The shape of protection elements 122e, 122f, 122g may be mostly determined by flexible frame 121, and may take various forms, for example two ellipses 122e, two circles 122f, or two oblongs 122g, each such pair of protection elements covering two ureteral orifices 16.

Protection element 122 may be manufactured as part of the TBP device 20 (or 30), with different devices having different sizes or shapes of protection elements 122 to fit different patient anatomies. Alternatively, protection elements 122 may be added to TBP device 20 following the measurement procedure described above, and appropriately positioned so as to cover the orifices when the device is deployed, as shown in FIG. 12C.

Figure 12C:
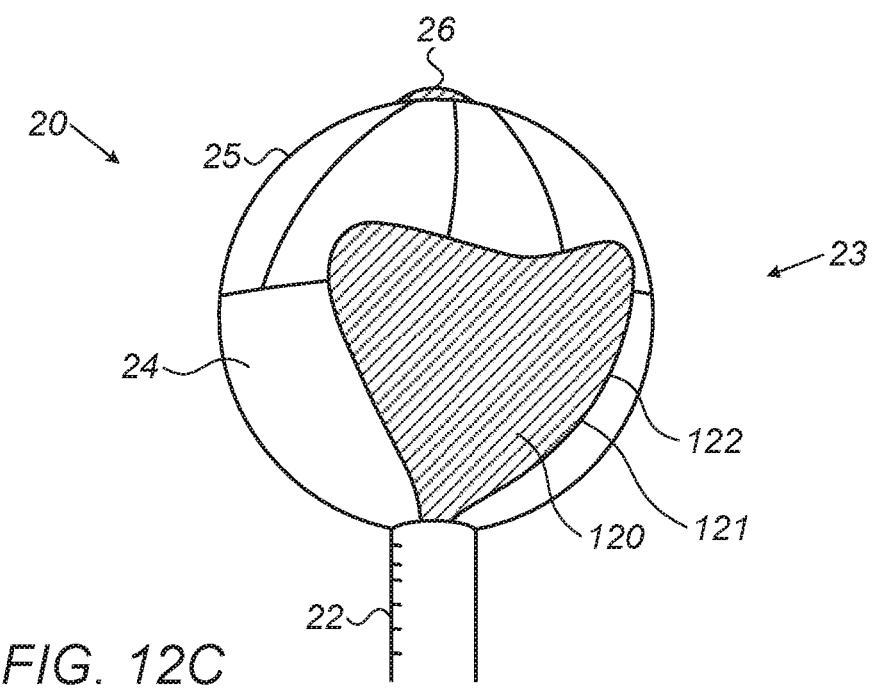
FIG. 12C is a schematic simplified three dimensional depiction of a protection element deployed with a TBP device, according to many embodiments.

More particularly, FIG. 12C is a simplified schematic three dimensional depiction of device 20 with protection element 122, in a deployed state. Protection element 122 may be seen extending out of the distal end of outer sheath 22 of TBP device 20. Protection element 122 may cover a part of electrode structure 25, thus preventing creation of a lesion in the bladder wall region which may be in contact with that part.

Protection element 122 may be an integral part of tool 23, and may, for example, be connected to the shaft of balloon 24, so that protection element 122 may be deployed out of outer sheath 22 and retracted back into it, together with tool 23.

Figure 12D:
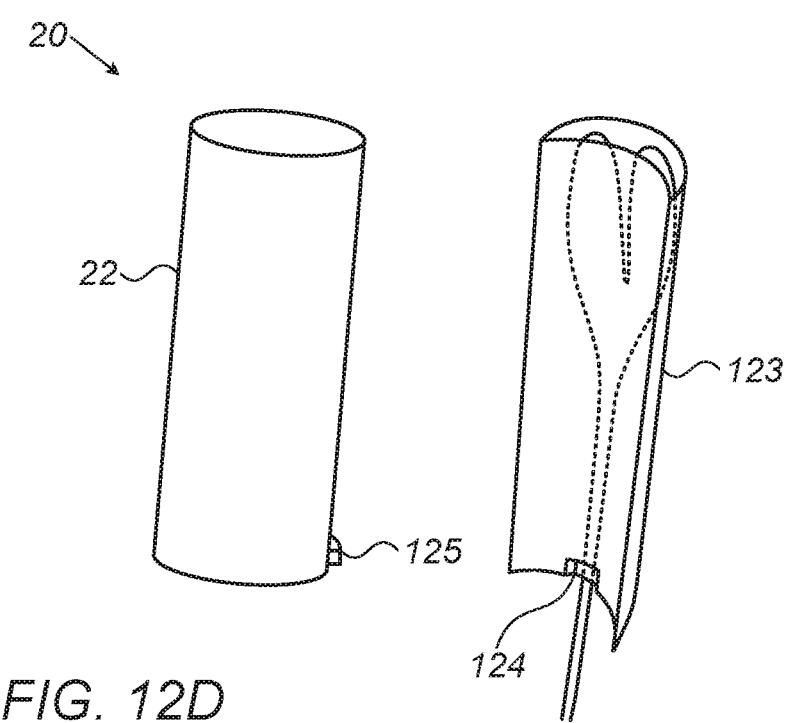
FIG. 12D is a schematic simplified three dimensional depiction of a protection element with a dedicated deployment sheath, according to many embodiments.

Alternatively, as shown in FIG. 12D, protection element 122 may be inserted separately from tool 23, for example alongside the outer surface of device 20.

More particularly, FIG. 12D is a simplified schematic three dimensional depiction of a protection element 122 inside a dedicated deployment sheath 123, which may be placed in the urethra 15 in parallel to the device shaft. Optionally, dedicated deployment sheath 123 may have a C shaped cross section, and may engulf outer sheath 22 of TBP device 20, adding only slightly to its outer diameter. Further optionally dedicated deployment sheath may have a notch 124 which fits to a protrusion 125 in the base of the device shaft, serving to align dedicated deployment sheath 123 with TBP device 20, such that protection element 122 is deployed at 6 o'clock of the deployed tool 23 (as seen in FIG. 12C).

In some embodiments, a thin insulating layer may be pre-applied over all the electrodes, effectively blocking them from conduction, and the operator may remove part of this protective layer, for example by peeling it off, only over the electrodes he wishes to actually activate. In some embodiments, the device controller may automatically detect which of the electrodes is covered and which is exposed (by the increased impedance of the former), and may selectively activate only the electrodes that have been exposed.

As shown in FIGS. 13A-13D, ureteral shields may be formed as "plugs" that are inserted into the ureteral orifices during cystoscopy before the procedure, and may be removed after the procedure.

More particularly, FIG. 13A is a simplified schematic front view of ureteral plug 131 comprising a circular insulation sheath 132 and a thin tube 133 perpendicularly extending from its center.

FIG. 13B is a simplified schematic side view of ureteral plug 131 showing the same elements as in FIG. 13A.

In an embodiment of ureteral plug 131 shown in FIGS. 13C-13D, a ureteral plug is described which may be configured to be inserted and pulled out of the bladder via a cystoscope sheath or even via a cystoscope working channel.

More particularly, FIG. 13C is a simplified schematic front view of a spiral ureteral plug 131a, comprising circular insulation sheath 132, thin tube 133 perpendicularly extending from its center, and wire spiral 134 having tube end 135 and free end 136. Tube end 135 of wire spiral 134 may be connected and continuous with thin tube 133. Free end 136 may have a further small bend to prevent its tip from being sharp. Spiral wire 134 may be formed of a nitinol or other shape memory alloy and may be configured to assume a circular shape when free. Circular insulation sheath 133 may typically be connected to spiral wire 134, such that when spiral wire 134 assumes it circular shape, circular insulation sheath 133 may create a flat circular shape. When pulled at free end 135, for example into a working channel of a cystoscope, spiral wire 134 can almost straighten out into a collapsed state.

FIG. 13D is a simplified schematic three-dimensional depiction of spiral ureteral plug 131a, depicting the same elements as in FIG. 13C.

In use, ureteral plug 131a in its collapsed state may be delivered into a bladder via a cystoscope, allowed to assume its circular shape, and then thin tube 133 may be inserted into a ureteral orifice 16 such that circular insulation sheath 133 may surround it and may protect it from ablation.

Figure 14B:
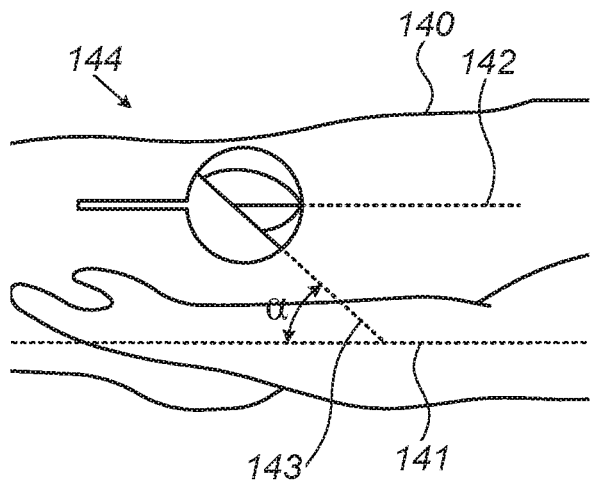
FIG. 14B a simplified schematic side view of a tilted base TBP device in its deployed and expanded state within a bladder, according to many embodiments.
Figure 14C:
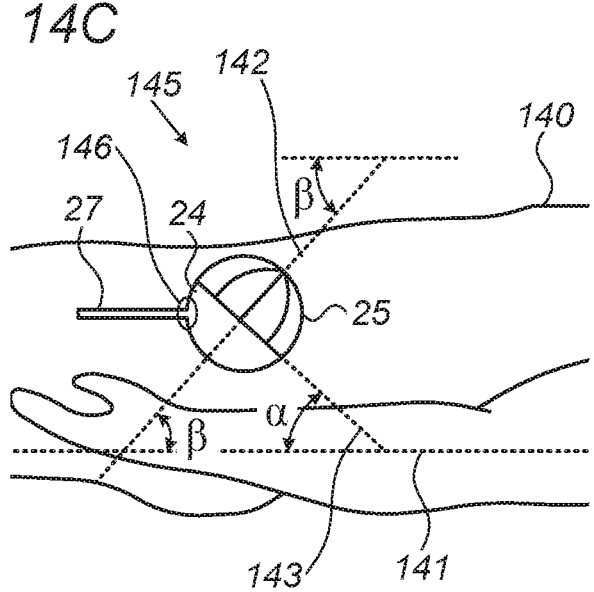
FIG. 14C is a simplified schematic side view of a tilted TBP device in its deployed and expanded state within a bladder, according to many embodiments.

In some embodiments described in FIGS. 14A-14C, the electrode arrangement previously described may be at least partially tilted relative to the longitudinal axis of the patient, to avoid ablating the ureteral orifices, and/or the intramural part of the ureter (which may obliquely run within the bladder wall up to ~1.5 cm from the ureteral orifices until exiting the bladder). Such tilting may involve the circumferential electrodes only, or both the circumferential electrodes and the longitudinal electrodes.

More particularly, FIG. 14A is a simplified schematic side view of a TBP device 20 (or 30) in its deployed and expanded state within a bladder, seen through the body of a patient 140.

Patient body 140 may have a longitudinal axis 141 extending along the body along the rostral-caudal direction (head to toes). The longitudinal axis of TBP device 20, typically corresponding to that of shaft 27 and external sheath 22, are typically parallel to patient body longitudinal axis 141 when the device is inserted into the patient's body. Electrode structure 25 of TBP device 20 may comprise longitudinal electrodes which may have longitudinal electrode axis 142. Electrode structure 25 of TBP device 20 may further comprise base axis 143. Base axis 143 may be defined by a plain connecting the proximal ends of the longitudinal electrodes of electrode structure 25, thus defining the most proximal regions where ablation can be performed. In some embodiments, TBP device 20 further comprises circumferential electrodes along base axis 143, but in some cases these may not be for defining base axis 143. Base axis 143 may be at an angle to patient body longitudinal axis 141.

In the previously described embodiments of TBP devices 20 or 30, longitudinal electrodes axis 142 may typically be substantially parallel to patient body longitudinal axis 141, and base axis 143 may be substantially perpendicular to patient body longitudinal axis 141, i.e. an angle α may typically be approximately 90 degrees.

FIG. 14B is a simplified schematic side view of a tilted base TBP device 144, which is an embodiment of TBP device 20 or 30, in its deployed and expanded state within a bladder, seen through the body of a patient 140. The same components seen in FIG. 14A are seen here with the exception that base axis 143 may be tilted relative to patient body longitudinal axis 141, thus the angle α may be substantially different from 90 degrees, typically less than 90 degrees. Note that base longitudinal electrodes axis 142 of tilted base device 144 may be parallel to patient body longitudinal axis 141.

FIG. 14C is a simplified schematic side view of a tilted TBP device 145, which may be similar in many respects to the TBP devices 20 and 30 described above, in its deployed and expanded state within a bladder, seen through the body of a patient 140. The same components seen in FIG. 14B are seen here with the exception that in addition to base axis 143 being tilted relative to patient body longitudinal axis 141, longitudinal electrodes axis 142 of tilted device 145 may form an angle β with patient body longitudinal axis 141. The angle β may typically be between 0 and 90 degrees. Since base axis 143 may typically be substantially perpendicular to longitudinal electrodes axis 142, the sum of angles α and β may typically be substantially 90 degrees. Another optional feature shown in FIG. 14C may be shaft hinge 146 connecting shaft 27 with expandable element 24.

In some embodiments, the angle α may be between 0 to 90 degrees. In some embodiments, the angle α may be set according to the volume of the expandable member, with smaller bladder volumes dictating a greater tilt (i.e., the angle α may be closer to 0 degrees), and larger bladder dictating smaller tilt (i.e., the angle α may be closer to 0 degrees). For example: bladder volumes of ~180 cc may require an angle α of ~45 degree whereas bladder volumes of ~250 cc may only require a ~25 degrees angle, to keep the ablation pattern away from the ureters. In some embodiments, the angle α may be set or chosen according to the previously measured ureteral orifice 16 distance from bladder outlet 15. In some embodiments, when the measured distance is above 30 mm, the expandable member may be inflated to ~250 cc (or a device having an expandable member of this volume may be chosen) and/or the electrodes may be tilted. In some embodiments, when the measured distance is above 45 mm, the expandable member may be chosen or inflated to ~250 cc, and the electrodes may be tilted to 20 to 50 degrees.

In some embodiments, the same device can accommodate for different filling volumes and/or different tilting angles. In some embodiments, the device may have a fixed expanded volume and/or fixed tilting angle, and the operator may choose the appropriate device or dimensions and tilt according to the needs as described above.

For technical reasons, it may typically be preferable that longitudinal electrodes axis 142, be at least somewhat aligned with shaft 27, to allow easier folding, deployment, and retrieval. Thus, it may be preferable to achieve the tilted pattern, with TBP devices in which longitudinal electrodes axis 142 may be substantially parallel to patient body longitudinal axis 141. In other words, it may be advantageous to be able to control angle α, and optionally change it after the device has been inserted into the patient's body, and prior to removal from the body.

In some embodiments, hinge 146 may be configured to create angle α by tilting expandable element 24 with electrode structure 25 relative to shaft 27. In these embodiments, TBP device 146 may be inserted into a patient's body with the longitudinal electrodes axis 142 parallel to patient's body longitudinal axis 141, and once in the bladder, tilting may be performed to change angle α. For example, hinge 146 may divide shaft 27 into two parts, a proximal part (closer to the operator), and a distal part. Both parts may be straight, but hinge 146 may create the desired tilting angle α between them. In these embodiments, the longitudinal electrodes may be substantially parallel to the distal part of the device (shaft) and may be tilted only in relation to the proximal shaft and the bladder axis.

In some embodiments, the hinge is a zone in shaft 27 that is more flexible than the rest of the shaft. For example, shaft 27 may be formed from nitinol or other shape memory alloy, and hinge 146 may comprise an area that was heat treated to bend to a certain angle in a deployed position, and return to a straight shape when inside external sheath 22. In some embodiments, in which the device may comprise an outer shaft and an inner shaft, the inner shaft may have a hinge, and the outer shaft may be straight and optionally substantially rigid, to facilitate retrieval of the inner shaft.

In some embodiments, the hinge zone may be adjacent to the end of the external shaft, so that the tip of the external shaft may be tilted once within the bladder. Then, the internal shaft (that may be somewhat flexible) may be pushed through the external shaft, assuming the tilt direction in relation to patient's body longitudinal axis 141.

In some embodiments, the device may be deployed in the bladder, until hinge 146 may pass bladder outlet 14, and bending may be performed only then.

Typically, the bladder may be pre-filled with fluid or air to a volume that exceeds the expanded device volume by at least 25%, to allow tilted deployment of the device. Only after the device is deployed at the desired position, the bladder may be drained to come into good contact with the device in the tilted position.

Typically, the distance from hinge 146 to the device distal tip, or atraumatic cap 26 (at the deployed, expanded state) may be in the rage of the diameter of a substantially full bladder, ranging from 4 cm to 8 cm, for example, 7 cm.

Alternatively, a straight TBP device may be used, without a hinge point, and the tilting angle may be achieved by titling entire shaft 27 in relation to patient's body longitudinal axis 141. Such tilting may be performed once the tip of the device has passed the bladder neck, and when the bladder is filled with air or fluid. The distal part of the device may then be inserted into the bladder at the required tilting angle, with the proximal device end angled posteriorly (thus the distal end may be angled anteriorly, as desired).

Figure 14D:
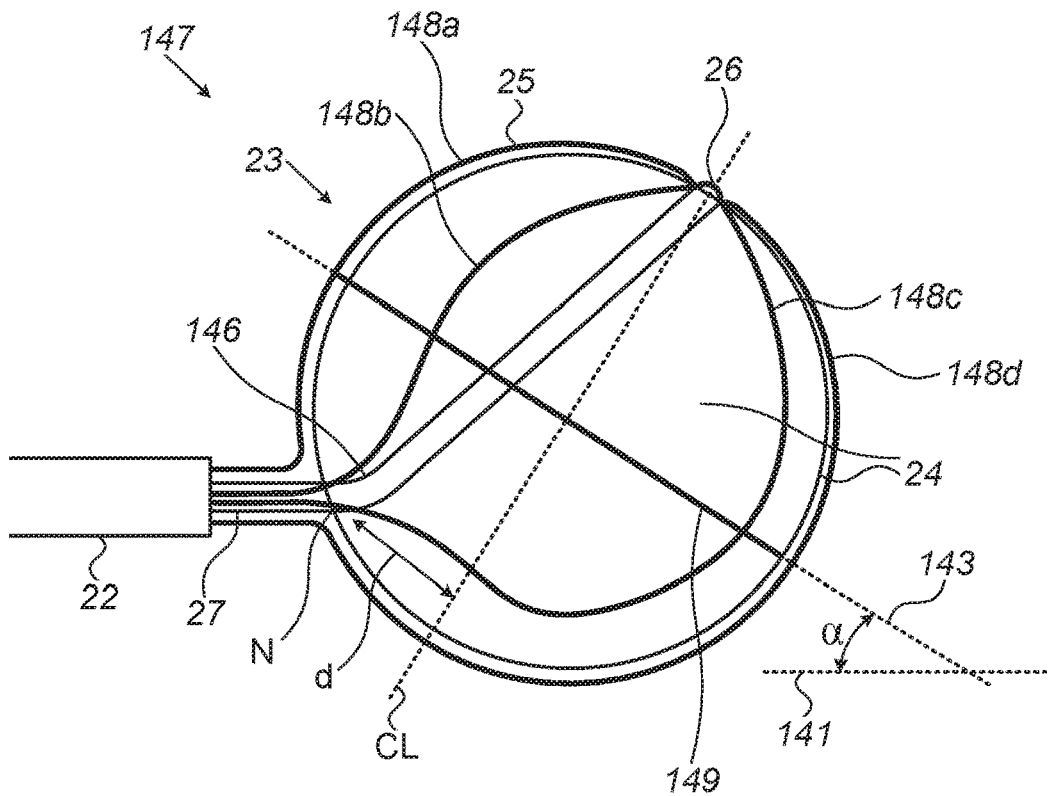
FIG. 14D is a simplified schematic side view of a non-concentric TBP device in its deployed and expanded state within, according to many embodiments.

FIG. 14D, describes an additional embodiment which may utilize a spherical expandable element which may be non-concentric, to produce the desired ablation pattern.

More particularly, FIG. 14D is a schematic simplified side view of non-concentric TBP device 147, depicting from proximal to distal: external sheath 22, shaft 27, hinge 146, expandable element 24, electrode structure 25 comprising longitudinal electrodes 148 and circumferential electrodes 149 having base axis 143, atraumatic cap 26, and patient longitudinal axis 141, proximal neck of expandable element (N), concentric line of expandable element (CL), and distance (d) between N and CL.

Particular aspects of the non-concentric TBP device 147 may include the following:

Hinge 146, which may typically be a flexible bend in shaft 27 as described above, may typically be located inside expandable element 24, as opposed to being proximal to its proximal neck N.

Expandable element 24, may typically be substantially spherical, or may have a shape more consistent with the actual shape of the urinary bladder. Regardless, CL is a concentric line pass from the distal tip of expandable element 24 at atraumatic cap 26, along its center. Importantly, to achieve the desired results, if an inflatable balloon is used for the expandable element 24, it may preferably be a non-compliant balloon.

Proximal neck N of expandable element 24, may typically be located at a point the surface of expandable element 24 that is anterior to where concentric line CL passes this surface. In other words, when viewing device 147 in side view, as in FIG. 14D, there may be a distance d between proximal neck N of expandable element 24, and the point where concentric line CL passes the perimeter of expandable element 24.

Electrode structure 25 may comprise longitudinal electrodes 148, which may be multiple (only four are shown in FIG. 14D for clarity, labeled 148*a*, 148*b*, 148*c*, 148*d*), and may comprise circumferential electrodes 149. Each longitudinal electrode 148 may be able to extend over expandable element 24 to a length determined by expansion of said expandable element, which may typically be different from that of adjacent longitudinal electrodes.

This nonconcentric mounting of expandable element 24 on shaft 27, with the position of hinge 146 distal to proximal neck N of expandable element 24, and each longitudinal electrode 148 being allowed to expand to a different extent over expandable element 24, may allow for creating angle α between base axis 149 and patient's body longitudinal axis 141, upon deployment of device 147 within a bladder.

Figure 14E:
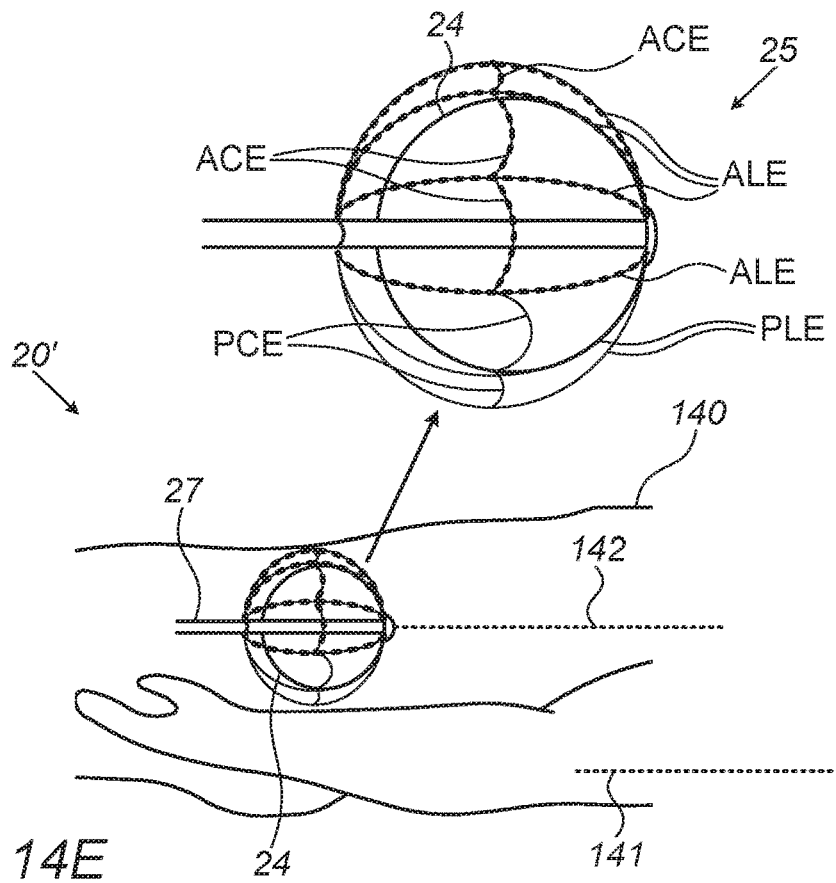
FIG. 14E is a simplified schematic side view of a localized ablation TBP device in its deployed and expanded state within a bladder, according to many embodiments.

In some embodiments described in FIG. 14E, a configuration similar to that previously described in FIG. 14A may be used, and protecting, or sparing, of parts of the bladder from ablation may be achieved by activating only specific electrodes (or electrode segments), for example those that are anterior to the bladder neck.

More particularly, FIG. 14E depicts TBP device 20', which may comprise shaft 27, expandable element 24, and electrode structure 25 which may comprise anterior longitudinal electrodes ALE and posterior longitudinal electrodes PLE, and optionally anterior circumferential electrodes ACE and posterior circumferential electrodes PCE.

TBP device 20' may be similar in most aspects to TBP device 20, with the exception that anterior electrodes ALE, and anterior circumferential electrodes ACE, located in its anterior side may be driven with energy during ablation, whereas posterior longitudinal electrodes PLE, and posterior circumferential electrodes PCE, may not be driven, and may only be used to provide structural integrity to electrode structure 25.

Thus, using this arrangement, anterior longitudinal electrodes ALE may create ablation lines running from bladder neck 14 to bladder dome 13, which may divide the anterior aspect of the bladder into separate slices, and anterior circumferential electrodes ACE may divide each of these segments into two.

The current disclosure further describes methods and devices to prevent the ablation lines from accidentally ablating zones that are below the desired defined circumferential ablation line, even in case the device did not fully deploy to its target volume.

Figure 15A:
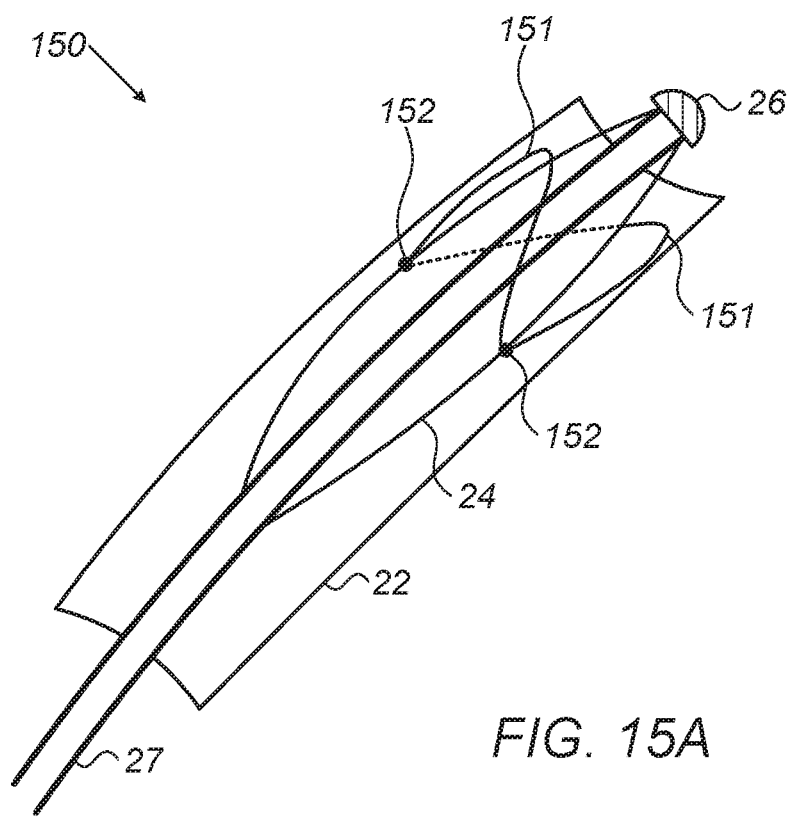
FIG. 15A is a simplified schematic longitudinal section of a foldable TBP device in its folded state, according to many embodiments
Figure 15B:
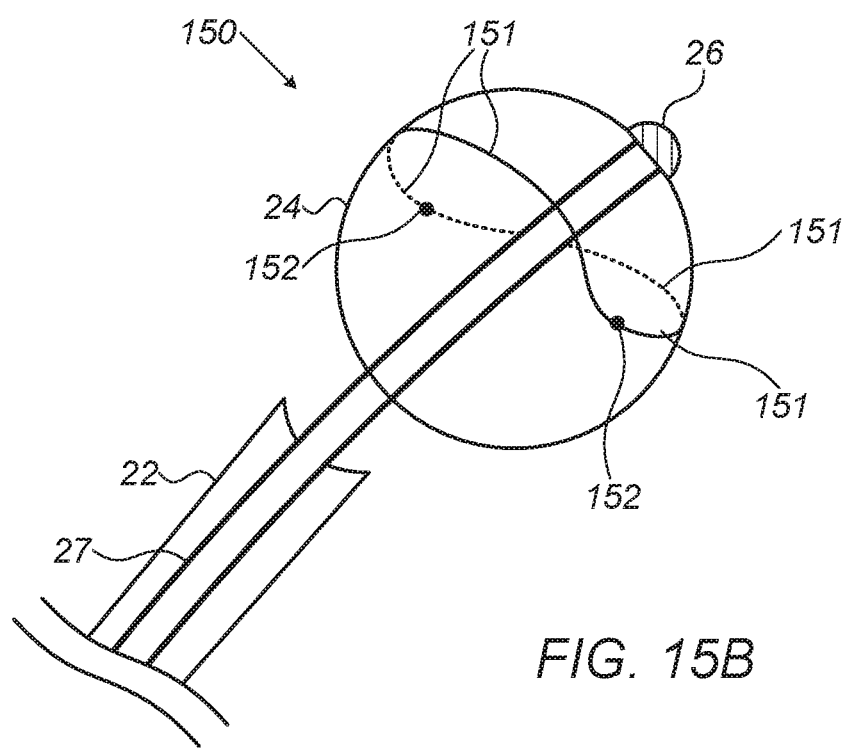
FIG. 15B is a simplified schematic longitudinal section of a foldable TBP device in its deployed, expanded state, according to many embodiments

FIGS. 15A-15B depict a TBP device having foldable circumferential electrodes.

More particularly, FIG. 15A is a simplified schematic longitudinal section of a foldable TBP device 150 in its folded state, comprising external sheath 22 and tool 23 comprising shaft 27, atraumatic cap 26, expandable element 24, and foldable circumferential electrodes 151 having connectors 152. There may be multiple foldable circumferential electrodes 151, although only two are depicted, for clarity. Connectors 152 may connect the ends of electrodes 151 directly to expandable element 24, or alternatively, to longitudinal electrodes as those described in previous embodiments, which may be part of electrode structure 25. Connectors 152 may typically be located above (i.e. distal to) the equator line of expandable element 24.

FIG. 15B is a simplified schematic longitudinal section of a foldable TBP device 150 in its deployed, expanded state.

Foldable circumferential electrodes 151 may typically comprise an elongate conductor which may include a wire or braid or any other type of conductor that may be sufficiently flexible to undergo the change from its folded state to its deployed state. Foldable circumferential electrodes 151 may be pre-folded on expandable member 24, with the fold directed distally, and may have a predetermined length consistent with the circumference of expandable element 24 at the level of connectors 152, such that when expandable element 24 expands above a specific volume, foldable circumferential electrodes 151 may be sufficiently stretched to remain above the circumferential line at the level of connectors 152, as seen in FIG. 15B. In this case, even if the device does not fully deploy, ablation may still remain above the circumferential line.

Figure 16:
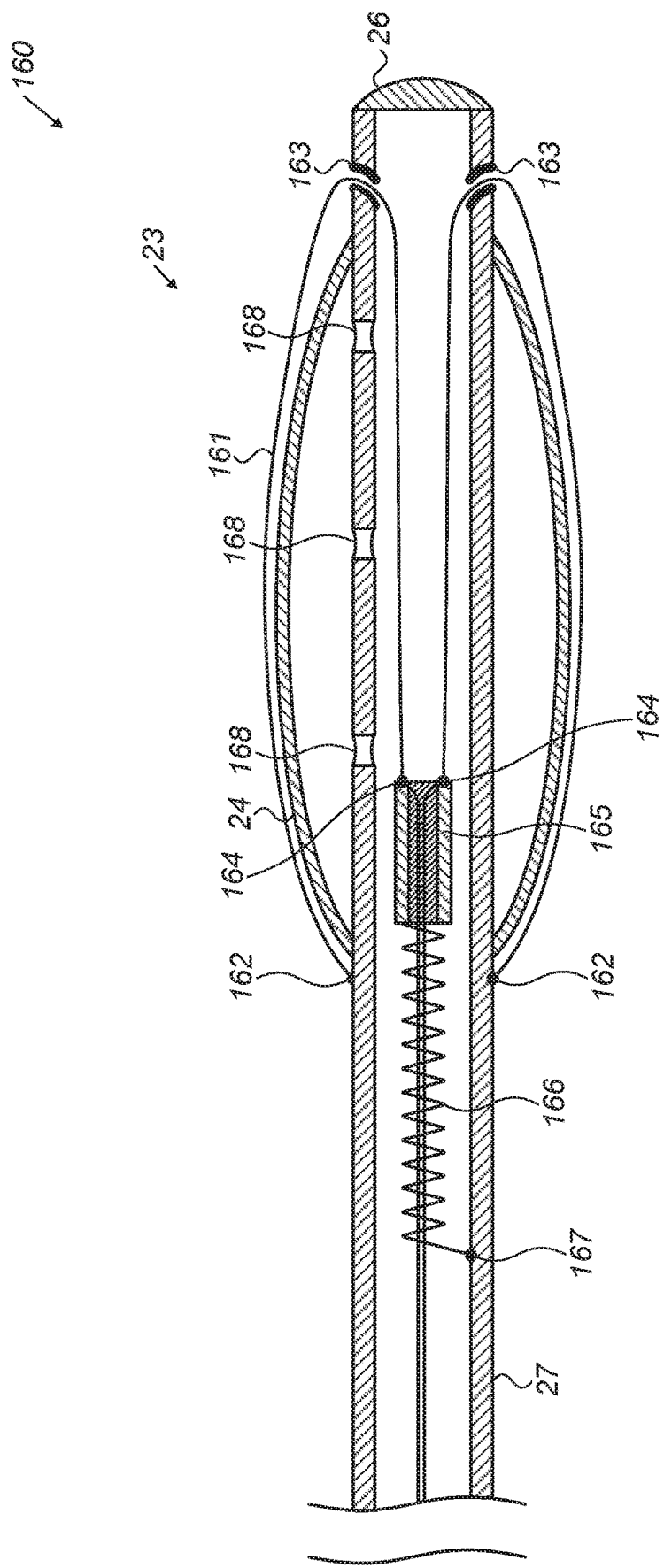
FIG. 16 is a simplified schematic longitudinal section of tool of a slidable TBP device in its crimped state, according to many embodiments.

FIG. 16 shows a TBP device, in which the longitudinal electrodes may be sliding electrodes, configured to slide out of the shaft of the device, through the upper end of the expandable element.

More particularly, FIG. 16 shows a simplified schematic longitudinal section of tool 23 of a slidable TBP device 160 in its crimped state, comprising shaft 27, atraumatic cap 26, expandable element 24, longitudinal slidable electrodes 161 having shaft connectors 162, passing distally along the outside of shaft 27, entering its lumen via openings 163, connecting at slider connectors 164 to slider 165, and projecting proximally therefrom. Slider 165 may typically be pulled proximally be spring 166, connected to shaft 27 at spring connector 167.

There may be multiple foldable slidable electrodes 161, although only two are depicted, for clarity. Slideable electrodes 161 may typically be made of a braided wire to prevent their kinking at sharp bends. Openings 163 may typically be lined with a low friction material or tube such as Teflon, to reduce force required for passing of slidable electrodes 161. Shaft 27 may further comprise apertures 168, to allow inflation of expandable member 24, in case it may be inflatable. In such case, there may additionally be a separate inflation lumen within shaft 27, or alternatively or additionally, openings 163 may be made fluid sealed to prevent leakage during inflation. Of note, although longitudinal electrodes 161 are herein described as longitudinal, they may create circumferential or other shaped lines over expandable member 24 in its expanded state, as was described in the previous disclosures included herein by reference.

In use, as expandable member 24 expands radially, it pulls slidable longitudinal electrodes 161 out of shaft 27 through openings 163, against the force of spring 166, allowing them to expand radially and appose the bladder wall. During contraction of expandable element 24, spring 166 pulls slidable electrodes 161 back into shaft 27.

The current disclosure further describes methods and devices to ascertain bladder integrity following the ablation procedure. In some embodiments, following the ablation, the bladder may be further inflated (with gas or liquid) and the pressure within the bladder may be monitored. In some embodiments, once the additional filling is performed, a substantially stable pressure may signify bladder integrity. In some embodiments, the pressure may be expected to rise during filling, plateau when filling stops, and then fluctuate—when a substantially stable average pressure during fluctuations signifies bladder integrity. In some embodiments the pressure after inflation may be monitored for at least 2 minutes before bladder integrity may be ascertained.

In some embodiments, the bladder may be filled with a fixed fluid volume, and then drained. Comparing the filled volume to the drained volume may teach of potential leaks. A volume smaller than expected may signify compromise of bladder integrity. In some embodiments the bladder may be filled with air, under ultrasound supervision, in order to detect any free air in the abdominal or pelvic compartments. In other embodiments the bladder may be filled with air and simple auscultation may be utilized to ascertain no compromise in bladder integrity (whistling sounds upon auscultation may indicate bladder wall breach).

In some embodiments, the step of filling the bladder may be an integral part of the electrode detaching stage. In other embodiments, the step of filling and then draining to ensure bladder integrity may be performed after the expandable member has been retrieved from the bladder.

In some embodiments, the electrodes used to deliver the energy to the tissue may themselves be designed to substantially and rapidly heat up during the ablation. In other words such electrodes may create the thermal effect in the tissue not only by resistive heating within the tissue, but also, or only, by heat transferred to the tissue from the electrodes, which may warm due to resistive heating within the electrodes. The inventors have found that heated electrodes can cause ablation lines that are thin and do not penetrate deeply into the bladder wall. In some embodiments, the desired depth of penetration of ablation may be less than 2 mm. In some embodiments, the heating of the electrodes may be achieved by using electrodes with a high resistance, such as certain metal alloys. Alternatively, in some embodiments, copper tungsten alloy may be used. In some embodiments, tungsten alloys may be used, or even almost pure tungsten. In some embodiments, zirconium copper may be used. In some embodiments, one or more alloys from the following list are used: chromium copper, beryllium copper, beryllium nickel copper, zirconium chromium copper, molybdenum.

In some embodiments, the high resistance of the electrodes may be achieved by using very thin metal filaments, braided with other filaments of lower conductance. In some embodiments electrodes made of the same materials as the electrodes used for resistance welding may be used to achieve the desired heating effect. In some embodiments silicon may be incorporated into the electrode, to achieve the desired effect.

In some embodiments, the electrodes used may be substantially thinner than commonly used RF ablation electrodes. While typical RF ablation electrodes will have a diameter of 2 mm to 7 mm, the current disclosure describes using electrodes that may be substantially thinner, having a diameter of less than 0.5 mm. Utilization of such thin electrodes may result with thin ablation lines, to preserve bladder tissue, while still achieving effective bladder partitioning. Utilization of such thin electrodes may also dramatically reduce the volume of the ablation lesion and with it the needed ablation time. Such short ablation times may be advantageous for patient comfort and increase the heat gradient within the tissue (heat conduction is in the bladder relatively slow). While reduction of this gradient may be usually desired and sought (in order to increase RF energy penetration into the tissue while minimizing extreme damage to superficial layers), the current disclosure describes purposely creating a steep gradient, to ensure the heating rapidly drops with distance, to make sure ablation may be relatively superficial (i.e., 1 mm-3 mm), and ensure that the bladder wall may not be penetrated and no damage may be afflicted to the adjacent tissues and/or organs.

In some embodiments, ablation may be applied simultaneously to several sites, so that the total ablation time may be reduced. In some embodiments, ablation lines having a total length of over 5 cm may be created simultaneously.

Various methods and devices for cooling the electrodes and tissue during ablation are described, with the goal of minimizing lesion width while enabling creation of sufficiently deep lesions.

In some embodiments, a balloon made of a thermoconductive material is used for expandable element 24. An example of such a material may be CoolPoly elastomer by Celanese Corporation, North Kingstown, R.I., USA. Filling the balloon with cooled liquid (e.g. water at 5 degrees Celsius) may allow rapid transfer of heat generated around the electrodes during ablation to the balloon, thus cooling the electrodes and adjacent tissue and minimizing lesion width while increasing depth. Furthermore, the cooling of the ablated tissue may induce reflex bladder contraction, improving the contact between the bladder and the device.

In another embodiment, the balloon may include microscopic holes at specific areas, for example along the electrodes, such that cooled fluid (e.g. distilled water at 5 degrees Celsius) percolates out of the balloon, optionally only above a specific inflation pressure, and this fluid may be drained through the external sheath 22.

In another embodiment, the cooled fluid may flow out of the device from an opening in its shaft at one point (e.g. distal end) and may be drained at another point (e.g. proximal end).

In yet another embodiment, precooling of the bladder may be performed by instillation of cooled fluid either directly or inside a balloon of the ablation device, and providing sufficient time for the superficial bladder tissues to cool before ablation.

In some embodiments, the methods and devices described may be used to create tissue lines having a decreased diffusion capacity across them. In some embodiments, the decreases in diffusion may be particularly prominent for large molecules such as proteins and peptides (and less so for smaller molecules such as oxygen or $CO_2$). In some embodiments, this decreased diffusion may effectively block or diminish paracrine signaling across the created lines. It is believed by the inventors that the reduced cellularity and increased fibrosis and scarring within these created lines may cause a physical barrier for paracrine activities by increasing the distance between adjacent paracrine cells to a distance that is above the maximal effective distance for paracrine activity. In some embodiments, this distance may be above 400 micrometers. In some embodiments, this disruption to diffusion creates disturbance to paracrine activities by reducing the diffusion of paracrine signaling molecules across the fibrotic lines.

In some embodiments, the reduced diffusion lines may be used to reduce the diffusion and dissemination of therapeutic molecules applied to the bladder tissue. In some embodiments, the therapeutic molecule may be botulinum toxin. In these embodiments, the reduced diffusion lines may be created to localize the applied toxin to a certain part of the bladder only, to reduce the risk of undesirable generalized bladder flaccidity and reduce the risk of urinary retention and/or increased residual volumes. In some embodiments, longitudinal lines may be created to create longitudinal bladder zones that are thus "spared" form diffusion of the therapeutic molecule (such as botulinum toxin or other bladder relaxant), and act as untreated bladder zones, to maintain bladder emptying, reduce residual volume and decrease the chances for urinary tract infection.

In some embodiments, the reduced diffusion lines may be used to reduce the diffusion of a chemotherapy agent injected into the bladder wall, to effectively limit the spread of the agent to adjacent unaffected bladder tissue. In some embodiments, such lines of reduced diffusion may be created around a tumor before the agent may be injected at the tumor site, to reduce diffusion of the agent away from the site, to increase the effective dose at the site, and to protect the normal tissue.

In some embodiments, the reduced diffusion lines may be created to reduce the translocation of cells across the lines. In some embodiments, these lines may be created to disturb the dissemination of cancerous cells across the lines. In some embodiments, such tissue lines may be created around a tumor, or around the bed of a tumor that has been resected, to prevent the tumor from spreading through the tissue.

In some embodiments, these ablation lines may be used to damage the microvascular plexus that lies under the endothelium (sub endothelial plexus) and/or the deeper mucosal plexus that lies just under the mucosa. These plexuses comprise many anastomoses, and interrupting them may interrupt paracrine communications across the ablation lines, allowing the creation of isolated bladder areas with reduced blood supply and reduced blood clearance. In some embodiments, the reduction in blood supply is used to attenuate the contraction of the bladder zone, to treat overactive bladder. In some embodiments, the reduction in blood supply is applied to reduce the growth of tumor tissue in the affected bladder zone.

Figure 17:
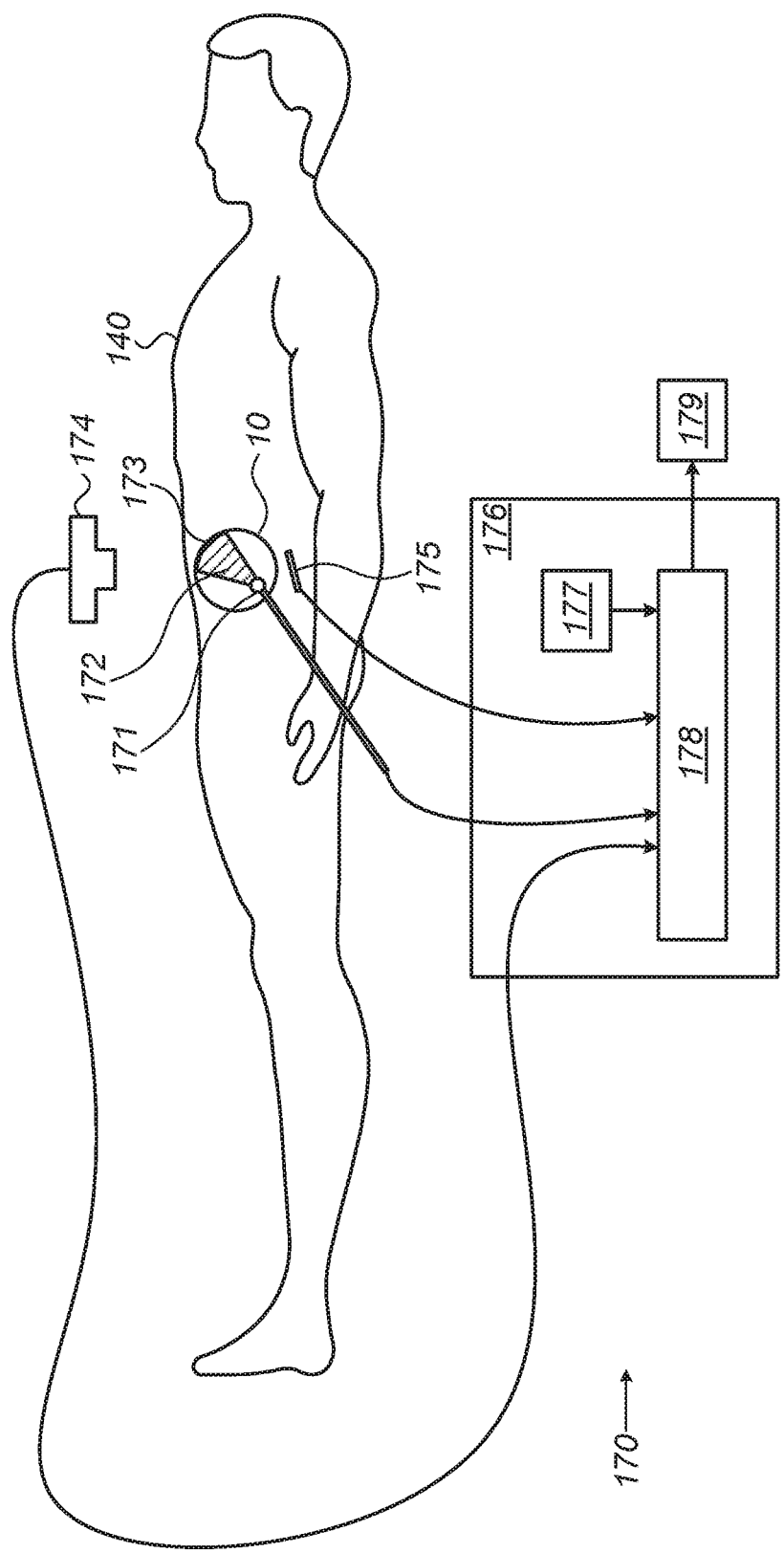
FIG. 17 is a schematic illustration of a diagnostic system, according to many embodiments.

Another system for diagnosing a medical condition of a urinary bladder is shown in FIG. 17.

More particularly, FIG. 17 is a schematic illustration of a patient's body 140 having a bladder 10, and diagnostic system 170 which may comprise internal imaging means 171 having a field of view 172, and optionally a projected grid 173, external imaging means 174, and optionally other sensors 175, processor 176, database 177, and algorithm 178 having output 179.

In some embodiments, internal imaging means 171 may comprise several cameras or lenses configured to jointly obtain a panoramic view of the whole interior surface area of a bladder 10. In some embodiments, internal imaging means 171 may comprise a "fish eye" lens at the end of a cystoscope. Narrow Band Imaging may be used to obtain a higher fidelity image. Identification of bladder wall movement, and more specifically micromotions of the bladder wall, may be further enhanced by the creation of markings on the inner bladder wall by sprinkling the bladder wall with visually prominent dye or biocompatible particles such as carbon particles. Alternatively or in combination, a pattern of dots or a grid may be projected on the inner bladder wall by a miniature projector within the imaging device.

In some embodiments, external imaging means 174 may be used to simultaneously monitor abdominal organ movements, activity, or pressure changes. This may be done in order to correlate this activity with the information obtained from within the bladder by internal imaging means 171, in order to eliminate artifacts caused by respiratory movements, intestinal activity, or external compression of the abdomen. In some embodiments, an external video camera or infrared camera filming the abdomen is used. In another embodiment, ultrasound monitoring of the abdomen is used, optionally using 3D ultrasound, optionally employing several probes at the same time. In some embodiments, other sensors 175 are additionally used, for example for monitoring abdominal pressure using a rectal or vaginal pressure sensor. Other sensors 175 may optionally additionally comprise other monitoring means for example ECG, saturation monitor, respirations monitor, motion detector, or any other source of physiologic parameters.

Data from internal imaging means 171, external imaging means 174, and other sensors 175, may be collected by processor 176 which analyzes it using an algorithm stored in a non-transient machine-readable medium 178. The algorithm 178 may use image analysis software to detect bladder micromotions and contractions based on data from internal imaging means 171. The algorithm 178 may further use data from external imaging means 174 and other sensors 175 to verify the accuracy or credibility of the detected activity. The algorithm 178 may, for example, use cancel data acquired by internal imaging means 171 during a period when an external imaging means 174 comprising a camera detects that the patient's abdomen was accidentally moved by a physician, or when an external imaging means 174 comprising an ultrasound system detects intense intestinal peristalsis. Alternatively or in combination, the algorithm 178 may subtract activity detected external to the bladder from activity detected within the bladder, and may provide the net activity of the bladder. This net activity may be displayed as a video for the assessment of a physician. The algorithm 178 may further compare this detected net activity to a database of normal activity, and may detect abnormalities in activity. The algorithm 178 may provide output 179 which may include any of the above mentioned video display of net activity, an alert, or a diagnosis based on detected abnormalities.

TABLE 1

| Reference number and figure element correspondence | |
|---|---|
| Reference Number | Element Name |
| 10 | Urinary bladder |
| 11 | Bladder wall |
| 12 | Bladder lumen |
| 13 | Bladder apex |
| 14 | Bladder outlet |
| 15 | Urethra |
| 16 | Ureteral orifice |
| 17 | Ureter |
| 18 | Ablation pattern |
| 19 | Electrically isolated zone |
| L | Longitudinal line |
| C | Circumferential line |
| T | Trigone |
| 20 | TBP device |
| 21 | Handle |
| 22 | Outer sheath |
| 23 | Tool/inner part(s) |
| 24 | Expandable element |
| 25 | Electrode structure |
| 26 | Atraumatic cap |
| 27 | Shaft |
| 30 | TBP-lavage device |
| 31 | Mucus layer |
| 32 | Nozzle |
| 33 | Central lumen |
| 34 | Outer lumen |
| 35 | Opening(s) |
| 36 | Jet |
| 41 | Baseline phase |
| 42 | Contact phase |
| 43 | Initial phase |
| 44 | Urothelium breach phase |
| 45 | Tissue warming phase |
| 46 | Disconnection phase |
| 47 | Post procedure phase |
| 51 | CNF baseline phase |
| 52 | CNF contact phase |
| 53 | CNF initial phase |
| 54 | CNF urothelium breach phase |
| 55 | CNF tissue warming phase |
| 56 | CNF disconnection phase |
| 57 | CNF post procedure phase |
| 60 | TBP flowchart |
| 70 | Ruler |
| 71 | Cystoscope |
| 72 | Hook |
| 80 | Triangular Measurement Tool (TMT) |
| 81 | Hollow tubes |
| 82 | Wire |
| 83 | Sheath |

TABLE 1-continued

Reference number and figure element correspondence

| Reference Number | Element Name |
| --- | --- |
| 90 | Inflatable Measurement Tool (IMT) |
| 91 | Shaft |
| 92 | Valve |
| 93 | Port |
| 94 | Cap |
| 95 | Aperture(s) |
| 96 | Measurement balloon |
| 97 | Sheath |
| 98 | Port |
| 99 | Gasket |
| 100 | Marking(s) |
| 101 | Grid |
| 120 | Insulating material |
| 121 | Flexible frame |
| 122a | Triangle shield |
| 122b | Oblong shield |
| 122c | Heart shaped shield |
| 122d | V shaped shield |
| 122e | (Two) ellipses shield |
| 122f | (Two) circles shield |
| 122g | (Two) oblongs shield |
| 123 | Dedicated deployment sheath |
| 124 | Notch |
| 125 | Protrusion |
| 131 | Ureteral plug |
| 131 | Spiral ureteral plug |
| 132 | Circular insulation sheath |
| 133 | Thin tube |
| 134 | Wire spiral |
| 135 | Tube end |
| 136 | Free end |
| 140 | Patient body |
| 141 | Longitudinal axis of patient body |
| 142 | Longitudinal electrode axis |
| 143 | Base angle |
| 144 | Tilted base TBP device |
| 145 | Tilted TBP device |
| 146 | Hinge |
| 147 | Nonconcentric TBP device |
| N | Proximal neck of expandable element |
| CL | Concentric line of expandable element |
| d | Distance from N to CL |
| AE | Anterior electrode(s) |
| PE | Posterior electrode(s) |
| 20' | Anterior ablation device |
| ALE | Anterior longitudinal electrode(s) |
| PLE | Posterior longitudinal electrode(s) |
| ACE | Anterior circumferential electrode(s) |
| PCE | Posterior circumferential electrode(s) |
| 150 | Foldable TBP device |
| 151 | Foldable circumferential electrode(s) |
| 152 | Connector(s) |
| 160 | Slidable TBP device |
| 161 | Slidable electrode(s) |
| 162 | Shaft connector(s) |
| 163 | Opening(s) |
| 164 | Slider connector(s) |
| 165 | Slider |
| 166 | Slider spring |
| 167 | Spring connector |
| 168 | Aperture(s) |
| 170 | Diagnostic system |
| 171 | Internal imaging source |
| 172 | Field of view |
| 173 | Projected grid |
| 174 | External imaging system |
| 175 | Other sensor(s) |
| 176 | Processor |
| 177 | Database |
| 178 | Algorithm (stored in non-transient mach readable medium) |
| 179 | Output |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of treating a disorder in a urinary bladder, the method comprising:
   creating a predetermined pattern of electrically isolated tissue regions having reduced electrical propagation in an inner wall of the urinary bladder such that electrical propagation through the urinary bladder as a whole is reduced,
   wherein creating the predetermined pattern of electrically isolated tissue regions comprises (i) advancing a tissue modification device through the urethra to reach the urinary bladder, (ii) expanding an expandable member disposed at the end of the distal end of the tissue modification device within the urinary bladder such than an outer surface of the expandable member contacts the inner wall of the urinary bladder, and (iii) ablating the inner wall of the urinary bladder with at least one elongate conductor positioned at the outer surface of the expandable member contacting the inner wall, wherein the inner wall of the urinary bladder is ablated to modify one or more of sub-endothelial tissue or mucosal tissue of the inner wall of the urinary bladder; and
   minimizing ablation of one or more non-targeted areas of the inner wall of the urinary bladder as the predetermined pattern of electrically isolated tissue regions is created.

2. The method of claim 1, wherein minimizing ablation of the one or more non-targeted areas of the inner wall of the urinary bladder comprises shielding the one or more non-targeted areas of the inner wall of the urinary bladder from ablation.

3. The method of claim 1, wherein the one or more non-targeted areas of the inner wall of the urinary bladder comprise a ureteral orifice.

4. The method of claim 3, wherein the one or more non-targeted areas of the inner wall of the urinary bladder comprise a ureteral orifice, and wherein the ureteral orifice is shielded with an electrically or thermally insulative shield or plug.

5. The method of claim 4, wherein the electrically or thermally insulative shield is disposed on the outer surface of the expandable member.

6. The method of claim 4, wherein the electrically or thermally insulative shield has a triangular shape, an oblong shape, a heart shape, a V-shape, a circular shape, or an elliptical shape.

7. The method of claim 1, wherein the predetermined pattern of electrically isolated tissue regions comprises one or more of at least one circumferential ablation line or at least one longitudinal ablation line in the inner wall of the urinary bladder.

8. The method of claim 7, wherein the predetermined pattern of electrically isolated tissue regions comprises one or more of at least one circumferential ablation line and at least one longitudinal ablation line in the inner wall of the urinary bladder.

9. The method of claim 8, wherein the at least one circumferential ablation line is inclined in relation to the at least one longitudinal ablation line.

10. The method of claim 9, wherein the at least one circumferential ablation line is inclined in relation to the at least one longitudinal ablation line between 15 to 90 degrees.

11. The method of claim 9, wherein the at least one circumferential ablation line is anteriorly inclined in relation to a long axis of a body of a patient.

12. The method of claim 9, wherein the at least one circumferential ablation line is inclined in relation to the at least one longitudinal ablation line based on a distance between a ureteral orifice and a bladder neck of the urinary bladder.

13. The method of claim 9, wherein the at least one longitudinal ablation line is distal to the at least one circumferential line.

14. The method of claim 1, further comprising measuring dimensions of the urinary bladder, wherein the pattern of electrically isolated tissue regions is predetermined based on the measured dimensions.

15. The method of claim 1, wherein minimizing ablation of the one or more non-targeted areas of the inner wall of the urinary bladder comprises avoiding ablation of the one or more non-targeted areas.

16. The method of claim 1, further comprising removing a mucus layer from an inner wall of the urinary bladder, wherein removal of the mucus layer facilitates the creation of the predetermined pattern of electrically isolated tissue regions.

17. The method of claim 16, wherein removing the mucus layer comprises introducing one or more of a high pressure fluid jet, a soap fluid, a solvent fluid, an acidic fluid, an enzymatic fluid, a pharmacological agent, an antiseptic fluid, a detergent, or mechanical remover to the bladder.

18. The method of claim 1, further comprising filling the bladder with a cold fluid to facilitate the creation of the predetermined pattern of electrically isolated tissue regions.

19. The method of claim 1, further comprising filling the bladder with a conductive fluid to facilitate the creation of the predetermined pattern of electrically isolated tissue regions.

20. The method of claim 1, further comprising filling the bladder with a non-conductive fluid to facilitate the creation of the predetermined pattern of electrically isolated tissue regions.

21. The method of claim 1, further comprising filling the bladder with a local anesthetic to facilitate the creation of the predetermined pattern of electrically isolated tissue regions.

22. The method of claim 1, further comprising visualizing the urinary bladder with a cystoscope prior to creating the predetermined pattern of electrically isolated tissue regions.

23. The method of claim 22, wherein visualizing the urinary bladder comprises assessing positions of ureteral orifices of the urinary bladder.

24. The method of claim 1, wherein the expandable member is expanded to a size based on a distance between a ureteral orifice and a bladder neck of the urinary bladder.

25. The method of claim 1, further comprising determining whether the at least one elongate conductor has contacted the inner wall sufficiently to ablate the inner wall.

26. The method of claim 25, wherein determining whether the at least one elongate conductor has contacted the inner wall comprises measuring an impedance of the inner wall with the at least one elongate conductor.

27. The method of claim 26, wherein measuring the impedance of the inner wall comprises measuring a change over time of the impedance.

28. The method of claim 27, wherein the change over time of the impedance comprises one or more of: an initial increase indicating contact between the at least one elongate conductor and the inner wall, a sequential rapid drop indicating a breach in an epithelium, a further reduction indicating tissue modification, and a third reduction indicating successful detachment of the at least one elongate conductor from the inner wall.

29. The method of claim 26, wherein the impedance of the inner wall is measured with the urinary bladder filled with a conductive fluid.

30. The method of claim 26, wherein the impedance of the inner wall is measured with the urinary bladder filled with a non-conductive fluid.

31. The method of claim 26, further comprising reducing or halting ablating by the at least one elongate conductor in response to the measured impedance.

32. The method of claim 31, wherein ablating is reduced or halted when the measured impedance is changed by a threshold amount.

33. The method of claim 32, further comprising indicating whether the urinary bladder is filled with a conductive or non-conductive fluid, wherein the threshold amount depends on whether the urinary bladder is filled with a conductive or non-conductive fluid.

34. The method of claim 1, wherein the expandable member comprises one or more markings denoting electrode positions and distance therefrom.

35. The method of claim 1, wherein the tissue modification device and the expandable member comprises a lumen configured for insertion of an endoscope there through while the expandable member is expanded.

* * * * *